(12) United States Patent
Christopherson et al.

(10) Patent No.: US 10,888,267 B2
(45) Date of Patent: Jan. 12, 2021

(54) METHOD OF TREATING SLEEP DISORDERED BREATHING

(71) Applicant: Inspire Medical Systems, Inc., Golden Valley, MN (US)

(72) Inventors: Mark A. Christopherson, Golden Valley, MN (US); Quan Ni, Golden Valley, MN (US); Timothy P. Herbert, Golden Valley, MN (US); John Rondoni, Golden Valley, MN (US)

(73) Assignee: Inspire Medical Systems, Inc., Golden Valley, MN (US)

( * ) Notice: Subject to any disclaimer, the term of this patent is extended or adjusted under 35 U.S.C. 154(b) by 179 days.

(21) Appl. No.: 15/239,057

(22) Filed: Aug. 17, 2016

(65) Prior Publication Data

US 2017/0128002 A1 May 11, 2017
US 2020/0146620 A9 May 14, 2020

Related U.S. Application Data

(60) Continuation of application No. 14/597,422, filed on Jan. 15, 2015, now abandoned, which is a division of
(Continued)

(51) Int. Cl.
*A61B 5/00* (2006.01)
*A61B 5/08* (2006.01)
(Continued)

(52) U.S. Cl.
CPC .......... *A61B 5/4818* (2013.01); *A61B 5/0205* (2013.01); *A61B 5/0538* (2013.01);
(Continued)

(58) Field of Classification Search
CPC ...... A61N 1/36; A61N 1/3601; A61B 5/0205; A61B 5/0803; A61B 5/0809; A61B 5/053;
(Continued)

(56) References Cited

U.S. PATENT DOCUMENTS 4,379,462 A 4/1983 Borkan
4,567,892 A 2/1986 Plicchi et al.
(Continued)

FOREIGN PATENT DOCUMENTS

JP H11504840 5/1999
JP H11514557 A 12/1999
(Continued)

OTHER PUBLICATIONS

Eisele Article—David W. Eisele, MD et al., "Tongue neuromuscular and direct hypoglossal nerve stimulation for obstructive sleep apnea," Otolaryngologic Clinics of North America, Otolayngol Clin N Am 36 (2003) 501-510 (10 pages).
(Continued)

*Primary Examiner* — Christopher A Flory
(74) *Attorney, Agent, or Firm* — Dicke, Billig & Czaja, PLLC

(57) ABSTRACT

A method includes applying electrical stimulation therapy via an electrode relative to an upper-airway-patency-related nerve to treat obstructive sleep apnea. A level of the electrical stimulation therapy is assessed.

23 Claims, 17 Drawing Sheets

Related U.S. Application Data application No. 13/130,287, filed as application No. PCT/US2009/065165 on Nov. 19, 2009, now Pat. No. 8,938,299.

(60) Provisional application No. 61/116,149, filed on Nov. 19, 2008.

(51) Int. Cl.
*A61N 1/36* (2006.01)
*A61B 5/0205* (2006.01)
*A61B 5/145* (2006.01)
*A61B 5/053* (2006.01)
*A61B 5/024* (2006.01)

(52) U.S. Cl.
CPC .......... *A61B 5/0803* (2013.01); *A61B 5/0809* (2013.01); *A61B 5/14542* (2013.01); *A61B 5/4836* (2013.01); *A61B 5/686* (2013.01); *A61B 5/7282* (2013.01); *A61N 1/3601* (2013.01); *A61B 5/024* (2013.01); *A61B 5/02405* (2013.01); *A61B 5/053* (2013.01); *A61B 2562/0214* (2013.01); *A61B 2562/0247* (2013.01)

(58) Field of Classification Search
CPC ... A61B 5/0535; A61B 5/4818; A61B 5/4836; A61B 5/0538; A61B 5/7282
USPC .......... 607/2, 9, 42; 600/301, 484, 529, 538, 600/546
See application file for complete search history.

(56) References Cited

U.S. PATENT DOCUMENTS

| | | |
|---|---|---|
| 4,573,481 A | 3/1986 | Bullara |
| 4,630,614 A | 12/1986 | Atlas |
| 4,813,431 A | 3/1989 | Brown |
| 2,960,133 A | 1/1990 | Hewson |
| 5,105,826 A | 4/1992 | Smits et al. |
| 5,121,754 A | 6/1992 | Mullett |
| 5,133,354 A | 7/1992 | Kallok |
| 5,134,995 A | 8/1992 | Gruenke et al. |
| 5,148,802 A | 9/1992 | Sanders et al. |
| 5,158,080 A | 10/1992 | Kallok |
| 5,167,229 A | 12/1992 | Peckham |
| 5,174,287 A | 12/1992 | Kallok et al. |
| 5,178,156 A | 1/1993 | Takishima et al. |
| 5,203,343 A | 4/1993 | Axe et al. |
| 5,211,173 A | 5/1993 | Kallok et al. |
| 5,215,082 A | 6/1993 | Kallok et al. |
| 5,233,983 A | 8/1993 | Markowitz |
| 5,238,006 A | 8/1993 | Markowitz |
| 5,239,995 A | 9/1993 | Estes et al. |
| 5,245,995 A | 9/1993 | Sullivan et al. |
| 5,265,624 A | 11/1993 | Bowman |
| 5,281,219 A | 1/1994 | Kallok |
| 5,300,094 A | 4/1994 | Kallok et al. |
| 5,335,657 A | 8/1994 | Terry, Jr. et al. |
| 5,344,438 A | 9/1994 | Testerman |
| 5,351,394 A | 10/1994 | Weinberg |
| 5,385,144 A | 1/1995 | Yamanishi et al. |
| 5,388,578 A | 2/1995 | Yomtov et al. |
| 5,398,682 A | 3/1995 | Lynn |
| 5,458,137 A | 10/1995 | Axe et al. |
| 5,483,969 A | 1/1996 | Testerman et al. |
| 5,485,851 A | 1/1996 | Erickson |
| 5,522,862 A | 6/1996 | Testerman et al. |
| 5,534,632 A | 6/1996 | Stein et al. |
| 5,531,778 A | 7/1996 | Maschino et al. |
| 5,540,731 A | 7/1996 | Testerman |
| 5,540,732 A | 7/1996 | Testerman |
| 5,540,733 A | 7/1996 | Testerman |
| 5,540,734 A | 7/1996 | Zabara |
| 5,546,952 A | 8/1996 | Erickson |
| 5,549,655 A | 8/1996 | Erickson |
| 5,588,439 A | 12/1996 | Hollub |
| 5,591,216 A | 1/1997 | Testerman et al. |
| 5,605,151 A | 2/1997 | Lynn |
| 5,645,053 A | 7/1997 | Remmers et al. |
| 5,671,733 A | 9/1997 | Raviv et al. |
| 5,769,084 A * | 6/1998 | Katz ..................... A61B 5/113 600/513 |
| 5,797,852 A | 8/1998 | Karakasoglu et al. |
| 5,823,187 A | 10/1998 | Estes et al. |
| 5,843,135 A | 12/1998 | Weijand et al. |
| 5,860,938 A | 1/1999 | Lafontaine |
| 5,895,360 A | 4/1999 | Christopherson et al. |
| 5,904,141 A | 5/1999 | Estes et al. |
| 5,916,221 A | 7/1999 | Miesel |
| 5,919,221 A | 7/1999 | Miesel |
| 5,944,680 A | 8/1999 | Christopherson et al. |
| 5,999,836 A | 12/1999 | Pardey et al. |
| 6,015,389 A | 1/2000 | Brown |
| 6,016,808 A | 1/2000 | Landis |
| 6,021,352 A | 2/2000 | Christopherson et al. |
| 6,041,780 A | 3/2000 | Richard et al. |
| 6,052,624 A | 4/2000 | Mann |
| 6,099,479 A | 8/2000 | Christopherson et al. |
| 6,120,441 A | 9/2000 | Griebel |
| 6,125,290 A | 9/2000 | Miesel |
| 6,125,291 A | 9/2000 | Miesel |
| 6,126,611 A | 10/2000 | Bourgeois et al. |
| 6,132,384 A | 10/2000 | Christopherson et al. |
| 6,134,459 A | 10/2000 | Roberts et al. |
| 6,144,866 A | 11/2000 | Miesel et al. |
| 6,172,772 B1 | 1/2001 | Steinle et al. |
| 6,181,961 B1 | 1/2001 | Prass |
| 6,198,952 B1 | 3/2001 | Miesel |
| 6,223,064 B1 | 4/2001 | Lynn et al. |
| 6,240,316 B1 | 5/2001 | Richmond et al. |
| 6,248,080 B1 | 6/2001 | Miesel et al. |
| 6,249,703 B1 | 6/2001 | Stanton et al. |
| 6,251,126 B1 | 6/2001 | Ottenhoff et al. |
| 6,269,269 B1 | 7/2001 | Ottenhoff et al. |
| 6,307,481 B1 | 10/2001 | Lehrman et al. |
| 6,309,350 B1 | 10/2001 | Van Tassel et al. |
| 6,314,324 B1 | 11/2001 | Lattner et al. |
| 6,342,039 B1 | 1/2002 | Lynn et al. |
| 6,345,202 B2 | 2/2002 | Richmond et al. |
| 6,361,494 B1 | 3/2002 | Lindenthaler |
| 6,393,325 B1 | 5/2002 | Mann |
| 6,449,507 B1 | 9/2002 | Hill et al. |
| 6,450,957 B1 | 9/2002 | Yoshimi et al. |
| 6,465,866 B2 | 9/2002 | Durand et al. |
| 6,522,928 B2 | 2/2003 | Whitehurst et al. |
| 6,532,388 B1 | 3/2003 | Hill et al. |
| 6,542,776 B1 | 4/2003 | Gordon et al. |
| 6,574,507 B1 | 6/2003 | Bonnet |
| 6,587,725 B1 | 7/2003 | Durand et al. |
| 6,606,521 B2 | 8/2003 | Paspa et al. |
| 6,609,016 B1 | 8/2003 | Lynn |
| 6,609,032 B1 | 8/2003 | Woods et al. |
| 6,629,527 B1 | 10/2003 | Estes et al. |
| 6,641,542 B2 | 11/2003 | Cho et al. |
| 6,645,143 B2 | 11/2003 | Van Tassel et al. |
| 6,647,289 B2 | 11/2003 | Prutchi |
| 6,651,652 B1 | 11/2003 | Ward |
| 6,654,634 B1 | 11/2003 | Prass |
| 6,665,560 B2 | 12/2003 | Becker et al. |
| 6,666,830 B1 | 12/2003 | Lehrman et al. |
| 6,689,068 B2 | 2/2004 | Hale et al. |
| 6,703,939 B2 | 3/2004 | Lehrman et al. |
| 6,718,208 B2 | 4/2004 | Hill et al. |
| 6,719,708 B1 | 4/2004 | Jansen |
| 6,731,976 B2 | 5/2004 | Penn et al. |
| 6,731,984 B2 | 5/2004 | Cho et al. |
| 6,735,471 B2 | 5/2004 | Hill et al. |
| 6,752,765 B1 | 6/2004 | Jensen et al. |
| 6,770,022 B2 | 8/2004 | Mechlenburg et al. |
| 6,773,404 B2 | 8/2004 | Poezevera et al. |
| 6,805,667 B2 | 10/2004 | Christopherson et al. |
| 6,811,538 B2 | 11/2004 | Westbrook et al. |

(56) References Cited

U.S. PATENT DOCUMENTS

| | | |
|---|---|---|
| 6,829,508 B2 | 12/2004 | Schulman et al. |
| 6,842,647 B1 | 1/2005 | Griffith et al. |
| 6,881,192 B1 | 4/2005 | Park |
| 6,890,306 B2 | 5/2005 | Poezevera |
| 6,893,405 B2 | 5/2005 | Kumar et al. |
| 6,904,320 B2 | 6/2005 | Park et al. |
| 6,907,293 B2 | 6/2005 | Grill |
| 6,928,324 B2 | 8/2005 | Park et al. |
| 6,935,335 B1 | 8/2005 | Lehrman et al. |
| 6,936,011 B2 | 8/2005 | Sheldon |
| 6,964,641 B2 | 11/2005 | Cho et al. |
| 6,978,171 B2 | 12/2005 | Goetz et al. |
| 6,988,498 B2 | 1/2006 | Berthon-Jones |
| 7,025,730 B2 | 4/2006 | Cho et al. |
| 7,041,049 B1 | 5/2006 | Raniere |
| 7,054,692 B1 | 5/2006 | Whitehurst et al. |
| 7,077,810 B2 | 7/2006 | Lange et al. |
| 7,081,095 B2 | 7/2006 | Lynn et al. |
| 7,082,331 B1 | 7/2006 | Park et al. |
| 7,082,336 B2 | 7/2006 | Ransbury et al. |
| 7,087,053 B2 | 8/2006 | Vanney |
| 7,117,036 B2 | 10/2006 | Florio |
| 7,128,717 B1 | 10/2006 | Thach et al. |
| 7,130,687 B2 | 10/2006 | Cho et al. |
| 7,145,461 B2 | 12/2006 | Lehrman et al. |
| 7,149,573 B2 | 12/2006 | Wang |
| 7,155,278 B2 | 12/2006 | King et al. |
| 7,160,252 B2 | 1/2007 | Cho et al. |
| 7,160,255 B2 | 1/2007 | Saadat |
| 7,167,743 B2 | 1/2007 | Heruth et al. |
| 7,174,215 B2 | 2/2007 | Bradley |
| 7,186,220 B2 | 3/2007 | Stahmann et al. |
| 7,187,978 B2 | 3/2007 | Malek et al. |
| 7,189,204 B2 | 3/2007 | Ni et al. |
| 7,195,594 B2 | 3/2007 | Eigler et al. |
| 7,200,440 B2 | 4/2007 | Kim et al. |
| 7,206,635 B2 | 4/2007 | Cho et al. |
| 7,212,862 B2 | 5/2007 | Park et al. |
| 7,252,640 B2 | 8/2007 | Ni et al. |
| 7,269,457 B2 | 9/2007 | Shafer et al. |
| 7,269,459 B1 | 9/2007 | Koh |
| 7,277,749 B2 | 10/2007 | Gordon et al. |
| 7,330,760 B2 | 2/2008 | Heruth et al. |
| 7,336,996 B2 | 2/2008 | Hartley et al. |
| 7,351,208 B2 | 4/2008 | Brodnick et al. |
| 7,366,572 B2 | 4/2008 | Heruth et al. |
| 7,371,220 B1 | 5/2008 | Koh et al. |
| 7,387,608 B2 | 6/2008 | Dunlop et al. |
| 7,395,113 B2 | 7/2008 | Heruth et al. |
| 7,396,333 B2 | 7/2008 | Stahmann et al. |
| 7,398,115 B2 | 7/2008 | Lynn |
| 7,422,015 B2 | 9/2008 | Delisle et al. |
| 7,438,686 B2 | 10/2008 | Cho et al. |
| 7,447,545 B2 | 11/2008 | Heruth et al. |
| 7,454,250 B1 | 11/2008 | Bjorling et al. |
| 7,463,928 B2 | 12/2008 | Lee et al. |
| 7,468,040 B2 | 12/2008 | Hartley et al. |
| 7,469,697 B2 | 12/2008 | Lee et al. |
| 7,473,227 B2 | 1/2009 | Hsu et al. |
| 7,491,181 B2 | 2/2009 | Heruth et al. |
| 7,509,164 B2 | 3/2009 | Jensen et al. |
| 7,510,531 B2 | 3/2009 | Lee et al. |
| 7,526,341 B2 | 4/2009 | Goetz et al. |
| 7,542,803 B2 | 6/2009 | Heruth et al. |
| 7,572,225 B2 | 8/2009 | Stahmann et al. |
| 7,590,455 B2 | 9/2009 | Heruth et al. |
| 7,591,265 B2 | 9/2009 | Lee et al. |
| 7,596,413 B2 | 9/2009 | Libbus et al. |
| 7,596,414 B2 | 9/2009 | Whitehurst et al. |
| 7,603,170 B2 | 10/2009 | Hatlestad et al. |
| 7,610,094 B2 | 10/2009 | Stahmann et al. |
| 7,634,315 B2 | 12/2009 | Cholette |
| 7,644,714 B2 | 1/2010 | Atkinson et al. |
| 7,662,105 B2 | 2/2010 | Hatlestad |
| 7,672,728 B2 | 3/2010 | Libbus et al. |
| 7,678,061 B2 | 3/2010 | Lee et al. |
| 7,680,537 B2 | 3/2010 | Stahmann et al. |
| 7,680,538 B2 | 3/2010 | Durand et al. |
| 7,702,385 B2 | 4/2010 | Moffitt et al. |
| 7,717,848 B2 | 5/2010 | Heruth et al. |
| 7,720,541 B2 | 5/2010 | Stahmann et al. |
| 7,725,195 B2 | 5/2010 | Lima et al. |
| 7,726,209 B2 | 6/2010 | Ruotiostenmaki |
| 7,734,340 B2 | 6/2010 | De Ridder |
| 7,734,350 B2 | 6/2010 | Dubnov et al. |
| 7,742,819 B2 | 6/2010 | Moffitt |
| 7,747,323 B2 | 6/2010 | Libbus et al. |
| 7,751,880 B1 | 7/2010 | Cholette |
| 7,757,690 B2 | 7/2010 | Stahmann et al. |
| 7,775,993 B2 | 8/2010 | Heruth et al. |
| 7,783,353 B2 | 8/2010 | Libbus et al. |
| 7,792,583 B2 | 9/2010 | Miesel et al. |
| 7,792,590 B1 | 9/2010 | Pianca et al. |
| 7,809,442 B2 | 10/2010 | Bolea et al. |
| 7,818,063 B2 | 10/2010 | Wallace et al. |
| 7,853,322 B2 | 12/2010 | Bourget et al. |
| 7,881,798 B2 | 2/2011 | Miesel et al. |
| 7,887,493 B2 | 2/2011 | Stahmann et al. |
| 7,908,013 B2 | 3/2011 | Miesel et al. |
| 7,917,230 B2 | 3/2011 | Bly |
| 7,942,822 B1 | 5/2011 | Koh |
| 7,957,797 B2 | 6/2011 | Bourget et al. |
| 7,957,809 B2 | 6/2011 | Bourget et al. |
| 7,979,128 B2 | 7/2011 | Tehrani et al. |
| 8,016,776 B2 | 9/2011 | Bourget et al. |
| 8,021,299 B2 | 9/2011 | Miesel et al. |
| 8,150,531 B2 | 4/2012 | Skelton |
| 8,160,711 B2 | 4/2012 | Tehrani et al. |
| 8,175,720 B2 | 5/2012 | Skelton et al. |
| 2001/0010010 A1 | 7/2001 | Richmond et al. |
| 2002/0010495 A1 | 1/2002 | Freed et al. |
| 2002/0049479 A1 | 4/2002 | Pitts |
| 2002/0128700 A1 | 9/2002 | Cross, Jr. |
| 2002/0156507 A1 | 10/2002 | Lindenthaler |
| 2002/0193697 A1 | 12/2002 | Cho et al. |
| 2003/0093128 A1 | 5/2003 | Freed et al. |
| 2003/0114895 A1 | 6/2003 | Gordon et al. |
| 2003/0114905 A1 | 6/2003 | Kuzma |
| 2003/0163059 A1 | 8/2003 | Poezevera et al. |
| 2003/0195571 A1 | 10/2003 | Burnes et al. |
| 2003/0216789 A1 | 11/2003 | Deem et al. |
| 2004/0015204 A1 | 1/2004 | Whitehurst et al. |
| 2004/0073272 A1 | 4/2004 | Knudson et al. |
| 2004/0111139 A1 | 6/2004 | McCreery |
| 2004/0116819 A1 | 6/2004 | Alt |
| 2004/0134496 A1* | 7/2004 | Cho ............... A61B 5/0205 128/204.23 |
| 2004/0162499 A1 | 8/2004 | Nagai et al. |
| 2004/0210261 A1 | 10/2004 | King et al. |
| 2004/0215288 A1 | 10/2004 | Lee et al. |
| 2004/0230278 A1 | 11/2004 | Dahl et al. |
| 2004/0260310 A1 | 12/2004 | Harris |
| 2005/0004610 A1 | 1/2005 | Kim et al. |
| 2005/0043765 A1 | 1/2005 | Goetz et al. |
| 2005/0042589 A1 | 2/2005 | Hatlestad et al. |
| 2005/0043772 A1 | 2/2005 | Stahmann et al. |
| 2005/0065566 A1 | 3/2005 | Hartley et al. |
| 2005/0074741 A1 | 4/2005 | Lee et al. |
| 2005/0076908 A1 | 4/2005 | Lee et al. |
| 2005/0080348 A1 | 4/2005 | Stahmann et al. |
| 2005/0080461 A1 | 4/2005 | Stahmann et al. |
| 2005/0081847 A1 | 4/2005 | Lee et al. |
| 2005/0085865 A1 | 4/2005 | Tehrani |
| 2005/0085866 A1 | 4/2005 | Tehrani |
| 2005/0085868 A1 | 4/2005 | Tehrani et al. |
| 2005/0085869 A1 | 4/2005 | Tehrani et al. |
| 2005/0085874 A1 | 4/2005 | Davis et al. |
| 2005/0101833 A1 | 5/2005 | Hsu et al. |
| 2005/0107838 A1 | 5/2005 | Levett et al. |
| 2005/0113710 A1 | 5/2005 | Stahmann et al. |
| 2005/0115561 A1 | 6/2005 | Stahmann et al. |
| 2005/0145246 A1 | 7/2005 | Hartley et al. |
| 2005/0165457 A1 | 7/2005 | Benser et al. |
| 2005/0182457 A1 | 8/2005 | Thorpe |

(56) References Cited

U.S. PATENT DOCUMENTS

| | | |
|---|---|---|
| 2005/0197588 A1* | 9/2005 | Freeberg .............. A61B 5/0031 600/529 |
| 2005/0209513 A1 | 9/2005 | Heruth et al. |
| 2005/0209643 A1 | 9/2005 | Heruth et al. |
| 2005/0222503 A1 | 10/2005 | Dunlop et al. |
| 2005/0234523 A1 | 10/2005 | Levin et al. |
| 2005/0251216 A1 | 11/2005 | Hill et al. |
| 2005/0261747 A1 | 11/2005 | Schuler et al. |
| 2005/0267380 A1 | 12/2005 | Poezevera |
| 2005/0267547 A1 | 12/2005 | Knudson et al. |
| 2005/0277844 A1 | 12/2005 | Strother et al. |
| 2005/0277999 A1 | 12/2005 | Strother et al. |
| 2005/0278000 A1 | 12/2005 | Strother et al. |
| 2006/0004429 A1 | 1/2006 | Mrva et al. |
| 2006/0030894 A1 | 2/2006 | Tehrani |
| 2006/0036294 A1 | 2/2006 | Tehrani |
| 2006/0052836 A1 | 3/2006 | Kim et al. |
| 2006/0058852 A1 | 3/2006 | Koh et al. |
| 2006/0064029 A1 | 3/2006 | Abboud |
| 2006/0079802 A1 | 4/2006 | Jensen et al. |
| 2006/0095088 A1 | 5/2006 | De Ridder |
| 2006/0103407 A1 | 5/2006 | Kakizawa et al. |
| 2006/0135886 A1 | 6/2006 | Lippert et al. |
| 2006/0142815 A1 | 6/2006 | Tehrani et al. |
| 2006/0167497 A1 | 7/2006 | Armstrong et al. |
| 2006/0184204 A1 | 8/2006 | He |
| 2006/0224209 A1 | 10/2006 | Meyer |
| 2006/0241506 A1 | 10/2006 | Melker et al. |
| 2006/0241708 A1 | 10/2006 | Boute |
| 2006/0247729 A1 | 11/2006 | Tehrani et al. |
| 2006/0259079 A1 | 11/2006 | King |
| 2006/0264777 A1 | 11/2006 | Drew |
| 2006/0266369 A1 | 11/2006 | Atkinson et al. |
| 2006/0271137 A1 | 11/2006 | Stanton-Hicks |
| 2006/0276701 A1 | 12/2006 | Ray |
| 2006/0282127 A1 | 12/2006 | Zealear |
| 2006/0282131 A1 | 12/2006 | Caparso et al. |
| 2006/0293723 A1 | 12/2006 | Whitehurst et al. |
| 2007/0021785 A1 | 1/2007 | Inman et al. |
| 2007/0027482 A1 | 2/2007 | Parnis et al. |
| 2007/0038265 A1 | 2/2007 | Tcheng et al. |
| 2007/1150022 | 6/2007 | Ujhazy et al. |
| 2007/0233204 A1 | 10/2007 | Lima et al. |
| 2007/0255379 A1 | 11/2007 | Williams et al. |
| 2008/0009685 A1 | 1/2008 | Kim et al. |
| 2008/0039904 A1 | 2/2008 | Bulkes |
| 2008/0046055 A1 | 2/2008 | Durand et al. |
| 2008/0064977 A1 | 3/2008 | Kelleher et al. |
| 2008/0103407 A1* | 5/2008 | Bolea .................. A61N 1/0556 600/529 |
| 2008/0103545 A1 | 5/2008 | Bolea et al. |
| 2008/0103570 A1 | 5/2008 | Gerber |
| 2008/0109046 A1 | 5/2008 | Lima et al. |
| 2008/0109048 A1 | 5/2008 | Moffitt |
| 2008/0132802 A1 | 6/2008 | Ni et al. |
| 2008/0294060 A1 | 11/2008 | Haro et al. |
| 2009/0024047 A1 | 1/2009 | Shipley et al. |
| 2009/0062882 A1 | 3/2009 | Zhang et al. |
| 2009/0112116 A1 | 4/2009 | Lee et al. |
| 2009/0118787 A1 | 5/2009 | Moffitt et al. |
| 2009/0234427 A1 | 9/2009 | Chinn et al. |
| 2009/0270707 A1 | 10/2009 | Alfoqaha et al. |
| 2009/0287279 A1 | 11/2009 | Parramon et al. |
| 2009/0308395 A1 | 12/2009 | Lee et al. |
| 2009/0326408 A1 | 12/2009 | Moon |
| 2010/0016749 A1 | 1/2010 | Atsma et al. |
| 2010/0094379 A1 | 1/2010 | Thacker et al. |
| 2010/0036285 A1 | 2/2010 | Govari et al. |
| 2010/0087896 A1* | 4/2010 | McCreery .............. A61B 5/0088 607/62 |
| 2010/0125310 A1 | 5/2010 | Wilson et al. |
| 2010/0125315 A1 | 5/2010 | Bradley et al. |
| 2010/0137931 A1 | 6/2010 | Hopper et al. |
| 2010/0137949 A1 | 6/2010 | Mazgalev et al. |
| 2010/0152553 A1 | 6/2010 | Ujhazy et al. |
| 2010/0174335 A1* | 7/2010 | Stahmann .......... A61N 1/36514 607/20 |
| 2010/0174341 A1 | 7/2010 | Bolea et al. |
| 2010/0198103 A1 | 8/2010 | Meadows et al. |
| 2010/0228133 A1 | 9/2010 | Averina et al. |
| 2010/0228317 A1 | 9/2010 | Libbus et al. |
| 2010/0241195 A1 | 9/2010 | Meadows et al. |
| 2010/0266210 A1 | 10/2010 | Parramon et al. |
| 2011/0061647 A1* | 3/2011 | Stahmann ............ A61B 5/0031 128/202.16 |
| 2011/0093036 A1 | 4/2011 | Mashiach |
| 2011/0112601 A1 | 5/2011 | Meadows et al. |
| 2011/0137197 A1 | 6/2011 | Stahmann et al. |
| 2011/0152965 A1 | 6/2011 | Mashiach |
| 2011/0202106 A1* | 8/2011 | Bolea .................... A61N 1/0556 607/42 |
| 2011/0264164 A1 | 10/2011 | Christopherson et al. |
| 2012/0010532 A1* | 1/2012 | Bolea .................... A61N 1/0556 600/590 |
| 2012/0010681 A1* | 1/2012 | Bolea .................... A61N 1/0556 607/42 |
| 2012/0130445 A1* | 5/2012 | Lee ....................... A61M 16/00 607/42 |
| 2013/0218230 A1* | 8/2013 | Meadows ............ A61B 5/4818 607/42 |
| 2013/0253627 A1* | 9/2013 | Meadows ............... A61N 1/025 607/118 |
| 2014/0236255 A1* | 8/2014 | Meadows ............ A61B 5/4818 607/42 |
| 2015/0119955 A1* | 4/2015 | Meadows ............... A61N 1/025 607/42 |

FOREIGN PATENT DOCUMENTS

| | | |
|---|---|---|
| JP | 2004529707 | 9/2004 |
| JP | 2004529707 A | 9/2004 |
| JP | 2006516100 | 6/2006 |
| JP | 2007502670 A | 2/2007 |
| JP | 2007117591 | 5/2007 |
| JP | 2007512086 | 5/2007 |
| JP | 2008543429 | 12/2008 |
| JP | 2012509155 A | 4/2012 |
| JP | 2014184338 A | 10/2014 |
| JP | 2016137280 A | 8/2016 |
| WO | 199714354 | 4/1997 |
| WO | 200066215 | 11/2000 |
| WO | 2002087433 | 11/2002 |
| WO | 2004032719 | 4/2004 |
| WO | 2004064634 | 8/2004 |
| WO | 2005018737 | 3/2005 |
| WO | 2005055802 | 6/2005 |
| WO | 2006047264 | 5/2006 |
| WO | 2006057734 | 6/2006 |
| WO | 2006102591 | 9/2006 |
| WO | 2007061902 A2 | 3/2007 |
| WO | 2007068284 | 6/2007 |
| WO | 2007140597 | 12/2007 |
| WO | 2008025155 | 3/2008 |
| WO | 2008048471 | 4/2008 |
| WO | 2009048580 | 4/2009 |
| WO | 2009048581 | 4/2009 |
| WO | 2009135138 | 11/2009 |
| WO | 2009135140 | 11/2009 |
| WO | 2009135142 | 11/2009 |
| WO | 2009140636 | 11/2009 |
| WO | 2010039853 | 4/2010 |
| WO | 2010117810 | 10/2010 |

OTHER PUBLICATIONS

Goodall Article—Eleanor V. Goodhall et al., "Position-Selective Activation of Peripheral Nerve Fibers with a Cuff Electrode," IEEE Transaction on Biomedical Engineering, vol. 43, No. 8, Aug. 1996, pp. 851-856.

Naples Article—Gregory G. Naples et al., "A Spiral Nerve Cuff Electrode for Peripheral Nerve Stimulation," 8088 IEEE Transac-

(56) References Cited

OTHER PUBLICATIONS tions on Biomedical Engineering, 35. Nov. 1988, No. 11, New York, NY, pp. 905-915.
Oliven Article—Arie Oliven et al., "Upper airway response to electrical stimulation of the genioglossus in obstructive sleep apnea," Journal of Applied Physiology, vol. 95, pp. 2023-2029, Nov. 2003, www.jap.physiology.org on Sep. 18, 2006. (8 pages).
Schwartz Article—Alan R. Schwartz MD et al., Theraputic Electrical Stimulation of the Hypoglossal Nerve in Obstructive Sleep Apnea, Arch Otolaryngol Head And Neck Surg., vol. 127, Oct. 2001, pp. 1216-1223. Copyright 2001 American Medical Association. (8 pages).
Mann Article—Eric A. Mann et al., "The Effect of Neuromuscular Stimulation of the Genioglossus on the Hypopharyngeal Airway", The American Laryngological, Rhinological and Otologican Society, Inc., Feb. 2002, pp. 351-356.
Office Action Summary, App. No. 2016-060573, 2 pages.

\* cited by examiner

| SLEEP STUDY PARAMETERS (402) | EVENTS (406) | IPG THERAPY PARAMETERS (408) | NIGHT OF WEEK (420) | TIME OF DAY (421) | SLEEP STAGE (422) | BODY POSTURE (423) | PATIENT FACTORS (424) |
|---|---|---|---|---|---|---|---|
| AIRFLOW AT NOSTRILS AND MOUTH (410) | APNEA (413) | AMPLITUDE PATTERN OF BIO-IMPEDANCE AND RESPIRATORY PRESSURE (416) | NIGHT OF WEEK | TIME OF DAY | SLEEP STAGE | BODY POSTURE | AGE, SEX, SMOKER, WEIGHT, NECK, HYPERTENSION |
| % ↓ EXTERNALLY MEASURED Sat O₂ (411) OVER TIME PERIOD | APNEA (414) | INTERNALLY MEASURED Sat O₂ (417) | NIGHT OF WEEK | TIME OF DAY | SLEEP STAGE | BODY POSTURE | AGE, SEX, SMOKER, WEIGHT, NECK, HYPERTENSION |
| N/A (412) | APNEA (415) | ↑ INTRA PLEURAL PRESSURE (418) | NIGHT OF WEEK | TIME OF DAY | SLEEP STAGE | BODY POSTURE | AGE, SEX, SMOKER, WEIGHT, NECK, HYPERTENSION |
| SLEEP STAGE (425) | APNEA | ARRAY OF IPG PARAMETERS HR, Sat O₂, BIO IMPEDANCE, RESPIRATORY PRESSURE | NIGHT OF WEEK | TIME OF DAY | N/A | BODY POSTURE | AGE, SEX, SMOKER, WEIGHT, NECK, HYPERTENSION |

Fig. 4F

| PATIENT | PSG | IPG | DEMO | RESPONSIVE RATING |
|---|---|---|---|---|
| JOE | PSG 1 | IPG 1 | AGE, ETC | 8 |
| FRED | PSG 2 | IPG 2 | AGE, ETC | 2 |
| SUE | PSG 3 | IPG 3 | AGE, ETC | 4 |
| RON | PSG 4 | IPG 4 | AGE, ETC | 9 |

METHOD OF TREATING SLEEP DISORDERED BREATHING

CROSS-REFERENCE TO RELATED APPLICATIONS

This application is a Continuation of U.S. Divisional application Ser. No. 14/597,422, entitled "METHOD OF TREATING SLEEP DISORDERED BREATHING", having a filing date of Jan. 15, 2015, which claims priority to U.S. patent application Ser. No. 13/130,287, entitled "SYSTEM FOR TREATING SLEEP DISORDERED BREATHING," having a filing date of Jun. 24, 2011, now U.S. Pat. No. 8,938,299, issued Jan. 20, 2015 which claims priority to Provisional U.S. Patent Application Ser. No. 61/116,149, entitled "METHOD OF TREATING SLEEP APNEA," having a filing date of Nov. 19, 2008, and also claims priority to PCT Application PCT/US2009/065165, entitled "METHOD OF TREATING SLEEP DISORDERED BREATHING," having a filing date of Nov. 19, 2009 and all of which are incorporated herein by reference.

BACKGROUND

The present disclosure relates generally to an implantable stimulation system for stimulating and monitoring soft tissue in a patient, and more particularly, the present disclosure relates to a method of automatically initiating and adjusting therapeutic treatment of sleep apneas.

Sleep apnea generally refers to the cessation of breathing during sleep. One type of sleep apnea, referred to as obstructive sleep apnea (OSA), is characterized by repetitive pauses in breathing during sleep due to the obstruction and/or collapse of the upper airway, and is usually accompanied by a reduction in blood oxygenation saturation.

One treatment for sleep disordered breathing behavior, such as obstructive sleep apneas and hypopneas, has included the delivery of electrical stimulation to the hypoglossal nerve, located in the neck region under the chin. Such stimulation therapy activates the upper airway muscles to maintain upper airway patency. In treatment of sleep apnea, increased respiratory effort resulting from the difficulty in breathing through an obstructed airway is avoided by synchronized stimulation of an upper airway muscle or muscle group that holds the airway open during the inspiratory phase of breathing. For example, the genioglossus muscle is stimulated during treatment of sleep apnea by a nerve electrode cuff placed around the hypoglossal nerve.

BRIEF DESCRIPTION OF THE DRAWINGS

Aspects and features of the present disclosure will be appreciated as the same becomes better understood by reference to the following detailed description of the embodiments of the present disclosure when considered in connection with the accompanying drawings, wherein:

FIG. 4F is a block diagram schematically illustrating a correlation profile between sleep study parameters and therapy parameters associated with an implantable pulse generator, according to an embodiment of the present disclosure;

DESCRIPTION OF EMBODIMENTS

The following detailed description is merely exemplary in nature and is not intended to limit the present disclosure or the application and uses of the present disclosure. Furthermore, there is no intention to be bound by any expressed or implied theory presented in the preceding technical field, background, or the following detailed description.

Figure 1:
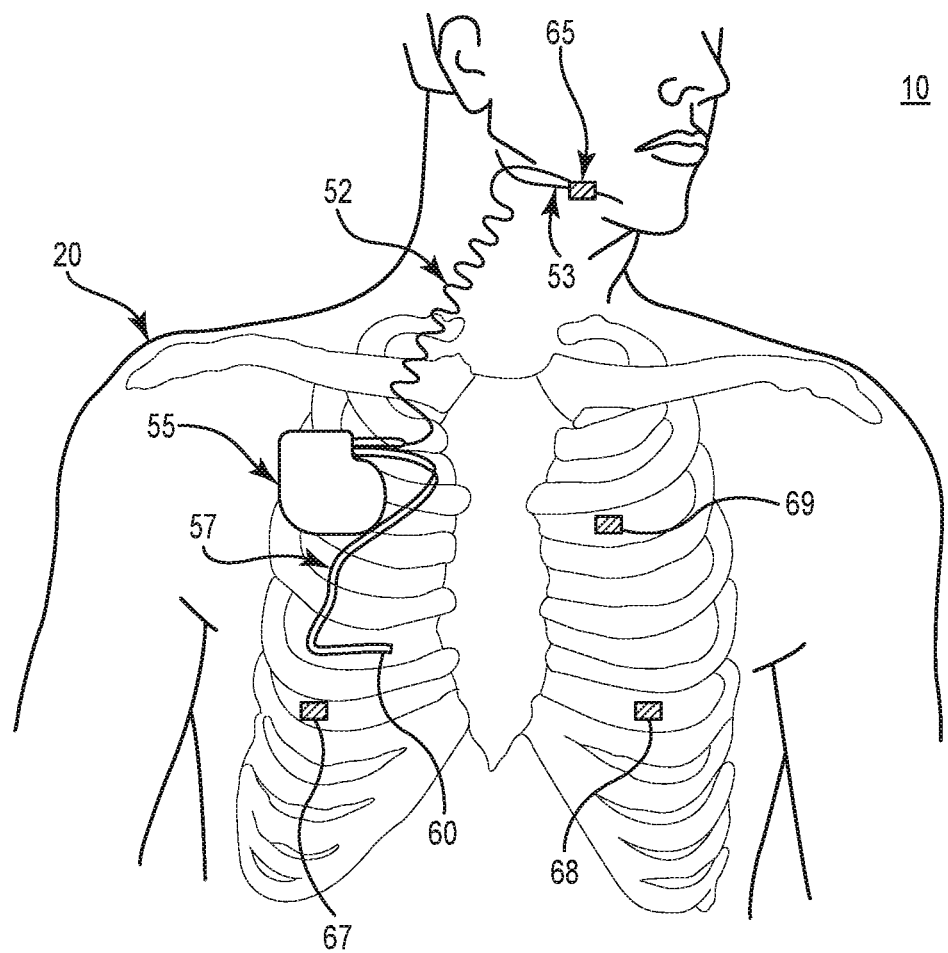
FIG. 1 is a schematic illustration of an implantable stimulation system, according to an embodiment of the present disclosure.

FIG. 1 is a schematic diagram of an implantable stimulation system, according to an embodiment of the present disclosure. The system is adapted to treat sleep disordered breathing behavior, such as obstructive sleep apnea, hypopnea, and/or central sleep apnea. As illustrated in FIG. 1, an example of an implantable stimulation system 10 according to one embodiment of the present disclosure includes an implantable pulse generator (IPG) 55, capable of being surgically positioned within a pectoral region of a patient 20, and a stimulation lead 52 electrically coupled with the IPG 55 via a connector (not shown) positioned within a connection port of the IPG 55. The lead 52 includes a nerve cuff electrode or electrode system 65 and extends from the IPG 55 so that the electrode system 65 is positioned in proximity to a desired nerve, such as the hypoglossal nerve 53 of the patient 20, to enable stimulation of the nerve 53, as described below in detail. It will be understood that in some embodiments, two leads 52 are provided with so that one lead 52 is implanted to be coupled relative to a nerve on a left side of the body and the other lead 52 is implanted to be coupled relative to a nerve on a second side of the body, as described in more detail below. An exemplary implantable stimulation system in which lead 52 may be utilized, for example, is described in U.S. Pat. No. 6,572,543 to Christopherson et al., which is incorporated herein by reference in its entirety. In this exemplary system, a sensor lead 57 electrically coupled to the IPG 55 and extends from the IPG 55 so that a sensor or transducer 60 can be positioned in the patient 20 for sensing of respiratory effort.

In some embodiments, system 10 also comprises additional sensors to obtain further physiologic data associated with respiratory functions. For example, system 10 may include various sensors (e.g., sensors 67, 68, 69 in FIG. 1) distributed about the chest area for measuring a transthoracic bio-impedance signal, an electrocardiogram (ECG) signal, or other respiratory-associated signals.

In some embodiments, the sensing and stimulation system for treating sleep disordered breathing behavior is a totally implantable system which provides therapeutic solutions for patients diagnosed with sleep disordered breathing. In other embodiments, one or more components of the system are not implanted in a body of the patient. A few non-limiting examples of such non-implanted components include external sensors (respiration, impedance, etc.), an external processing unit, or an external power source. Of course, it is further understood that the implanted portion(s) of the system provides a communication pathway to enable transmission of data and/or controls signals both to and from the implanted portions of the system relative to the external portions of the system. The communication pathway includes a radiofrequency (RF) telemetry link or other wireless communication protocols.

Whether partially implantable or totally implantable, the system is designed to stimulate the hypoglossal nerve (or other nerves related to affecting airway patency via tongue protrusion or other muscle contractions/relaxations) during inspiration to thereby prevent obstructions or occlusions in the upper airway during sleep. In one embodiment, the implantable system comprises an implantable pulse generator (IPG), a peripheral nerve cuff stimulation lead, and a pressure sensing lead.

Figure 2:
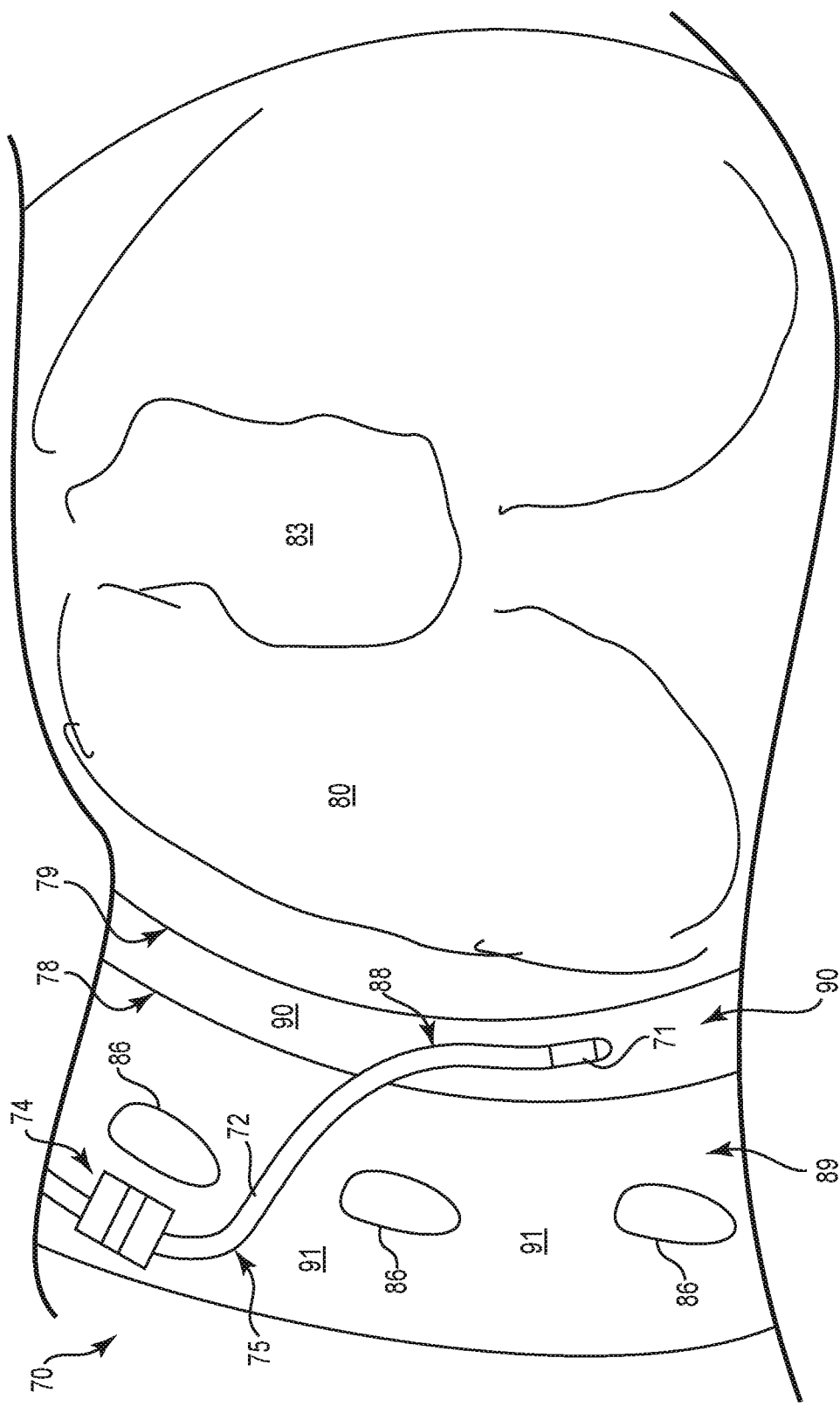
FIG. 2 is a schematic illustration of a method of placement for a respiratory pressure sensor, according to an embodiment of the present disclosure.

In one embodiment, the sensor 60 is a respiratory pressure sensor that is surgically implanted in a region that has pressure continuity with the pleura via an intrapleural placement or an extrapleural placement (including but not limited to an intercostal placement), as will be further described in association with FIG. 2. The location for placement of the sensor 60 is, at least in part, chosen as a function of a delay, i.e. the propagation time associated with a pressure waveform characteristic of respiratory effort propagating from the respiratory point of origin to the sensor position. The chosen location is also a function of the amount of filtering necessary to achieve a usable sensed signal at a particular location, i.e. the amount of filtering that is necessary to remove waveforms other than the waveform associated with the desired sensed characteristic, such as the filtering required to remove cardiac waveform activity, for example. The positioning of the sensor 60 enables the IPG 55 to receive respiratory effort waveform information and to use this information to control delivery of the therapy.

As schematically illustrated in FIG. 2, in one embodiment of the present disclosure, an implantable stimulation system 10 comprises a sensing system 70 including a lead 75 configured to place a respiratory pressure sensor 71 within an intrapleural space 90 so that sensor 71 is positioned in close proximity to the lung 80. In this arrangement, the sensor 71 becomes directly coupled relative to the respiratory pressures at the pleura. In another aspect, the intrapleural space 90 includes the cavity between the parietal pleura 78 and a pulmonary pleura 79. Finally, it will be understood that FIG. 2 illustrates generous spacing between adjacent anatomical structures for illustrative purposes.

In the one embodiment, lead 75 includes a lead body 72 that supports sensor 71 at its distal end and an anchor 74 (such as a wing-like fixation member) located at a more proximal portion of lead body 72. The anchor 74 ensures that sensor 71 remains positioned to orient the membrane portion of the sensor to face along the lung 80 subsequent to implantation of the sensor 71. The lead body 72 is positioned through an inter-costal space 91 into the pleural space 90 (with a position of sensor 71 and lead body 72 as indicated by reference numeral 88) so that the IPG 55 (FIG. 1) receives sensor waveforms from the sensor 71, thereby enabling the IPG 55 (FIG. 1) to deliver electrical stimulation synchronously with inspiration, according to a therapeutic treatment regimen in accordance with embodiments of the present disclosure.

As further illustrated by FIG. 2, the lead 75 will be inserted so that lead body 72 extends through the intercostal space (e.g. between two ribs 86) to position the sensor 71 for placement intrapleurally, as indicated generally via indicator 90. In one embodiment, the lead 75 incorporates a piezoelectric crystal mounted into a sealed housing and capable of monitoring intra-thoracic pressure associated with respiration. In other embodiments, monitoring the respiratory pressure comprises monitoring other physiological data indicative of respiratory pressure (in addition to or instead of monitoring intra-thoracic pressure). The sensor 71 is powered by the IPG 55 (FIG. 1) and the IPG 55 also contains internal circuitry to accept and process the respiration signal from the lead 75.

In one embodiment, the system includes a lead anchor 74 located remotely (by a distance of several centimeters or so) from where the sensor 71 is placed intrapleurally. Tissue movements on the sensor and lead can induce unwanted signal components as well as lead migration/dislodgement; therefore anchoring of the lead body 72, close to where the lead 75 enters the thoracic cavity is warranted. With this in mind, the anchor 74 will be sutured to a subcutaneous connective tissue, such as an intra-costal muscle or fascia during implant, and the anchor 74 is fixed or secured to the lead body 72 and not allowed to slide.

In other embodiments, the respiratory sensor 71 is placed external to the intrapleural space. In yet other embodiments, the respiratory sensor can be any one of an airflow sensor, a pressure sensor, a volume sensor, an accelerometer, an acoustic sensor, a temperature sensor, a mechanical strain sensor, or an effort sensor.

In one embodiment, sensing respiratory pressure is implemented in a manner substantially similar to the methods and systems of respiratory sensing disclosed in PCT Patent Application Number PCT/US2009/044207, entitled "Method and Apparatus for Sensing Respiratory Pressure in An Implantable Stimulation System," having a filing date of May 15, 2009, and which is incorporated herein by reference.

Figure 3A:
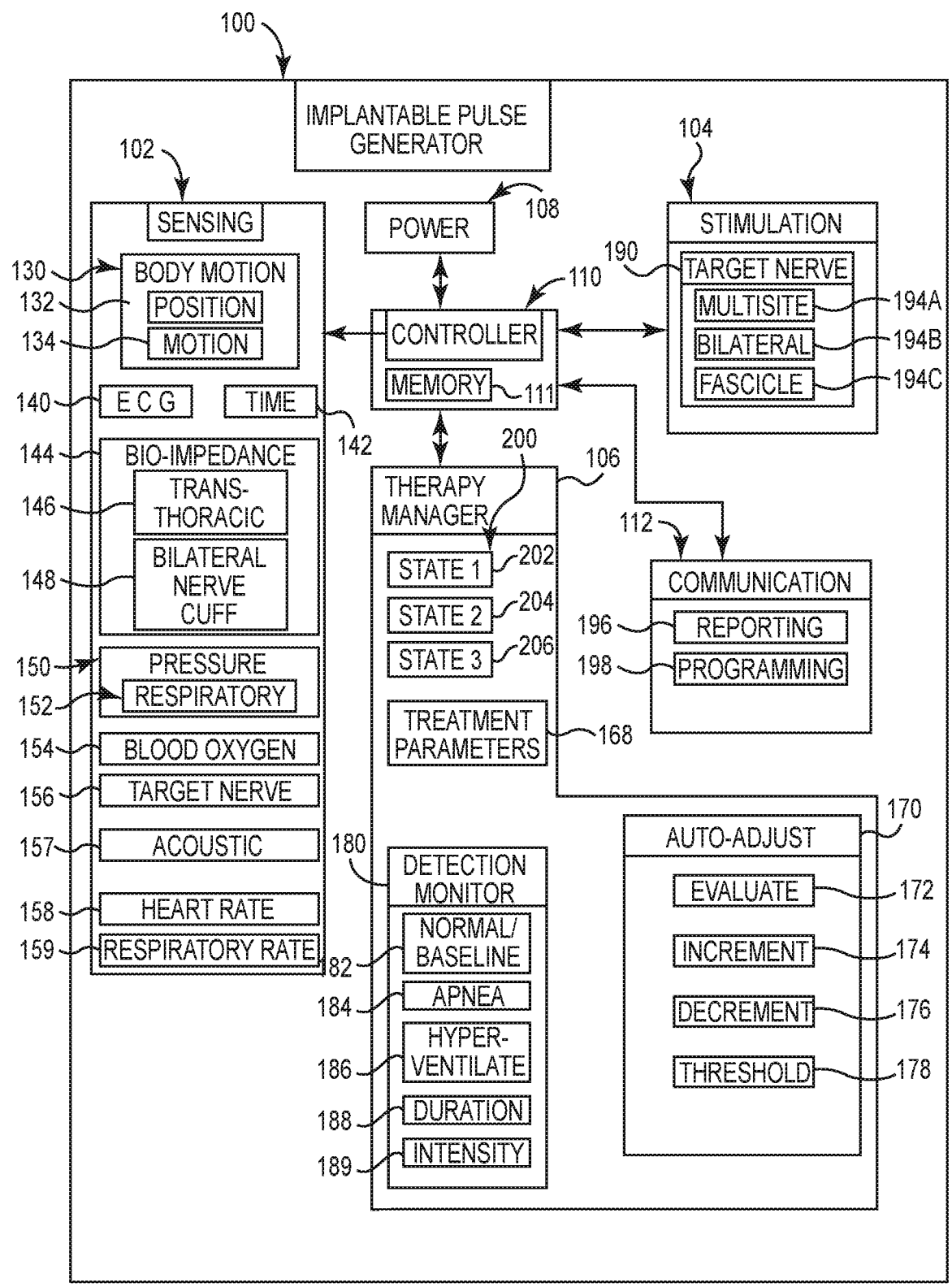
FIG. 3A is a block diagram of an implantable pulse generator, according to an embodiment of the present disclosure.

FIG. 3A is a block diagram schematically illustrating an implantable pulse generator (IPG) 100, according to one embodiment of the present disclosure. In one embodiment, IPG 100 comprises at least substantially the same features and attributes as IPG 55 of FIG. 1. As illustrated in FIG. 3A, IPG 100 includes a sensing module 102, a stimulation module 104, a therapy manager 106, a power management module 108, a controller 110 with a memory 111, and a communication module 112.

Components and methods of the present disclosure, including but not limited to memory module 111, may be implemented in hardware via a microprocessor, programmable logic, or state machine, in firmware, or in software within a given device. Components and methods of the present disclosure, including but not limited to memory module 111, may reside in software on one or more computer-readable media. The term computer-readable media as used herein is defined to include any kind of memory, volatile or non-volatile, such as floppy disks, hard disks, CD-ROMs, flash memory, read-only memory (ROM), and random access memory (RAM).

Via an array of parameters, the sensing module 102 of IPG 100 receives and tracks signals from various physiologic sensors in order to determine a respiratory state of a patient, such as whether or not the patient is asleep or awake, and other respiratory-associated indicators, etc. In one embodiment, at least some of the physiologic sensors are contained within or on a housing of the IPG and at least some of the physiologic sensors are external to the IPG. In any case, whether the physiologic sensors are external or internal to the IPG 100, the signals produced by those sensors are received and processed by the sensing module 102. In some embodiments, the sensing module 102 is contained within the IPG 100, although it will be understood that in other embodiments, at least a portion of the sensing module 102 can be external to a housing of the IPG 100 provided that communication is maintained between those external portions of sensing module 102 and the IPG 100.

For example, in one embodiment, the sensing module 102 comprises a body parameter 130, which includes at least one of a position-sensing component 132 or a motion-sensing component 134. In one embodiment, the motion-sensing component 134 tracks sensing of "seismic" activity (via an accelerometer or a piezoelectric transducer) that is indicative of walking, body motion, talking, etc. In another embodiment, the position-sensing component 132 tracks sensing of a body position or posture via an accelerometer or other transducer. In one embodiment, the position-sensing component distinguishes whether a patient is lying down in a generally horizontal position or standing up (or sitting up) in generally vertical position. In some embodiments, when the patient is in a generally horizontal position, the position-sensing component distinguishes between a supine position (i.e., lying on their back) and a lateral decubitus position (i.e., lying on their side). In some embodiments, body parameter 130 utilizes signals from both the position-sensing component 132 and the motion-sensing component 134.

Other parameters tracked via sensing module 102 include one or more of the following parameters: an ECG parameter 140; a time parameter 142; a bio-impedance parameter 144; a pressure parameter 150; a blood oxygen parameter 154 and/or a respiratory rate parameter 159. In one aspect, the ECG parameter 140 tracks electrocardiography information of the patient, and in some embodiments, a heart rate is tracked as a separate component via heart rate parameter 158. In one aspect, the pressure parameter 150 includes a respiratory pressure component 152, which includes a thoracic pressure component and/or other pressure component indicative of respiration of the patient. In one aspect, the time parameter 142 tracks elapsed time while in other aspects, the time parameter 142 tracks the time of day in addition to or instead of the elapsed time. In particular, in cooperation with a therapy manager 106, the time parameter 142 can be used to activate or deactivate a therapy regimen according to a time of day, as described later in association with at least FIGS. 4A and 8.

In some embodiments, the bio-impedance parameter 144 tracks measurements of bio-impedance of the patient. In one embodiment, the bio-impedance parameter 144 includes a trans-thoracic bio-impedance parameter that tracks a trans-thoracic bio-impedance, such as that described in association with sensors 67, 68, and 69 of FIG. 1, and as further described later in association at least FIGS. 5-7B. In another embodiment, the bio-impedance parameter 144 includes a bilateral nerve electrode (e.g. a cuff electrode) parameter that tracks a bio-impedance measured between a pair of nerve electrodes spaced apart from each other on opposite sides of the body, as described later in association with at least FIG. 5.

It is also understood that system 10 (FIG. 1) would include, or be connected to, the analogous physiologic sensor (e.g., LED-type tissue perfusion oxygen saturation) implanted within or attached to the body of the patient to provide data to each one of their respective parameters (e.g., blood oxygenation parameter 154) of the sensing module 102.

In some embodiments, sensing module 102 also includes a target nerve parameter 156 which represents physiologic data regarding the activity of a nerve to be stimulated, such as the hypoglossal nerve or other nerve related to influencing airway patency via muscle contraction.

In some embodiments, sensing module 102 also includes an acoustic sensing parameter 157 which represents physiologic data from respiratory airflow or cardiac activity that is sensed acoustically and that is indicative of respiratory effort.

In some embodiments, when data from obtained one or more of physiologic sensing parameters 140-144, 150-154, 157-159 of sensing module 102 reveals an ongoing inconsistent respiratory pattern, this information is used to indicate a potential waking state in which therapy should not be applied. In one aspect, the indication of a potential waking state is corroborated with information obtained via body parameter 130 prior to reaching a decision to abort a therapy or to delay the initiation of therapy. In further reference to FIG. 3A, therapy manager 106 of IPG 100 is configured to automatically control initiation of and/or adjustment of a sleep apnea therapy, in accordance with the principles of the present disclosure. In one embodiment, therapy manager 106 includes a multi-tier system 200 in which the IPG 100 will operate in one of three states of operation, including a first state 202, a second state 204, and a third state 206. This multi-tier system 200 will be later described in more detail in association with FIG. 4A.

Figure 4A:
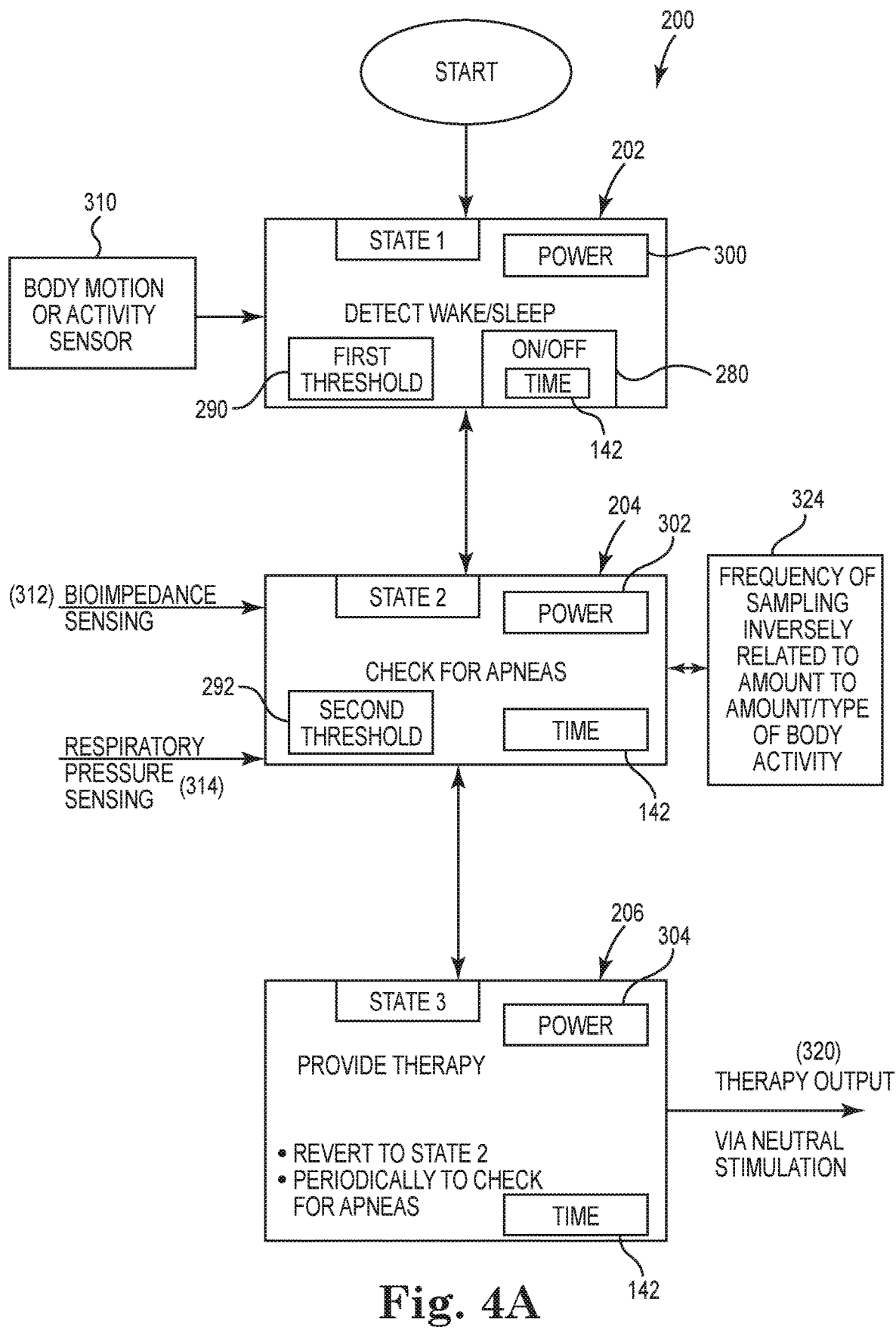
FIG. 4A is a block diagram of a multi-tier treatment system including different states of operation, according to an embodiment of the present disclosure.

In some embodiments, therapy manager 106 also includes an auto-titrate module 170 which may or may not operate in coordination with multi-tier system 200 (FIG. 4A). The auto-titrate module 170 is configured to direct the IPG 100 to automatically increment or decrement the level of therapy as implemented by various treatment parameters 168 (including but not limited to an amplitude, frequency, and/or pulse width of stimulation as well as a stimulation duty cycle and/or application of bilateral or unilateral stimulation, etc.) to maximize efficacy while minimizing power consumption and/or patient annoyance. In one aspect, efficacy is measured according to the number of apnea/hypopnea events and/or an apnea severity score (e.g. severity score parameter 759 in FIG. 9) that also incorporates a duration or an intensity (e.g., a decrease in blood oxygen) of each apnea/hypopnea event. Application of the auto-titrate module 170 is later described in more detail in association with at least FIGS. 8A, 8B, and 9.

With this in mind, in some embodiments, auto-titrate module 170 comprises an evaluate function 172, an increment function 174, a decrement function 176, and a threshold function 178. The evaluate function 172 is configured to evaluate the severity of sleep disordered breathing behavior both before and after the application of therapeutic nerve stimulation. The threshold function 178 enables setting a threshold of the severity of sleep disordered breathing that requires treatment by therapeutic nerve stimulation. If the severity of the sleep disordered breathing behavior falls below the threshold by a substantial portion, then auto-titrate module automatically decrements (decreases in one or more measured steps) the intensity of the nerve stimulation via decrement function 176. However, if the severity of the sleep disordered breathing behavior meets or exceeds the threshold, then auto-titrate module automatically increments (increases in one or more measured steps) the intensity of the nerve stimulation via increment function 174. In this way, the auto-titrate module 170 persistently evaluates and adjusts an intensity of therapeutic nerve stimulation so that enough stimulation is provided to treat the sleep disordered breathing but also so that unnecessary stimulation is avoided. Further application of the auto-titrate module 170 is later described in more detail in association with at least FIGS. 8A, 8B, and 9.

In some embodiments, therapy manager 106 also includes a detection monitor 180 which may or may cooperate with the multi-tier system 200 of FIG. 4A. In general terms, the detection monitor 180 observes, via sensing module 102, physiologic conditions of the patient to detect whether sleep disordered breathing is occurring, and based on such observations, initiate, adjust, or terminate a therapeutic nerve stimulation according to the general principles of the present disclosure. In one embodiment, the detection monitor 180 includes a baseline function 182, an apnea function 184, a hyperventilation function 186, a duration function 188, and an intensity function 190. The baseline function 182 tracks and determines a baseline breathing pattern for the patient in the absence of sleep disordered breathing. The apnea function 184 detects sleep disordered breathing, such as obstructive sleep apneas, hypopneas, and/or central sleep apneas, relative to the baseline breathing patterns of the patient. The hyperventilation function 186 is configured to assist identifying a sleep disordered breathing behavior based on parameters associated with a hyperventilation period following the sleep disordered breathing behavior. The duration function 188 tracks a duration of sleep disordered breathing events and/or duration of the ensuing hyperventilation, while the intensity function 190 tracks an intensity or severity of sleep disordered breathing events and/or of an intensity of the ensuing hyperventilation. In some embodiments, the functions 182-189 of the detection monitor 180 are implemented via the systems and methods described in association with at least FIGS. 3A-7C.

In one embodiment, controller 110 of IPG 100 comprises one or more processing units and associated memories 111 configured to generate control signals directing the operation of IPG 100, including the operation of at least sensing module 102, therapy manager 106, power module 108, stimulation module 104, and communication module 112. Accordingly, controller 110 is in communication with, and provides coordinated control over, each of the respective modules/managers 102-112 according to instructions in memory 111. In one aspect, in response to or based upon commands received via programming parameter 198 of communication module 112 and/or instructions contained in the memory 111 associated with controller 110 in response to physiologic data gathered via a sensing module 102, controller 110 generates control signals directing operation of stimulation module 104 to selectively control stimulation of a target nerve, such as the hypoglossal nerve, to restore airway patency and thereby reduce or eliminate apneic events. In one aspect, memory 111 stores a log of administered therapy and/or sensed physiologic data including data obtained during apnea/hypopnea events and data representing the efficacy of therapy during those events.

It is also understood that at least some of the components and parameters of the various modules and managers 102-112 could be located in a different pattern among the modules and managers 102-112 than shown and described in association with FIG. 3A.

For purposes of this application, the term "processing unit" shall mean a presently developed or future developed processing unit that executes sequences of instructions contained in a memory. Execution of the sequences of instructions causes the processing unit to perform steps such as generating control signals. The instructions may be loaded in a random access memory (RAM) for execution by the processing unit from a read only memory (ROM), a mass storage device, or some other persistent storage, as represented by a memory 111 associated with controller 110. In other embodiments, hard wired circuitry may be used in place of or in combination with software instructions to implement the functions described. For example, controller 110 may be embodied as part of one or more application-specific integrated circuits (ASICs). Unless otherwise specifically noted, the controller is not limited to any specific combination of hardware circuitry and software, nor limited to any particular source for the instructions executed by the processing unit.

In general terms, the stimulation module 104 of IPG 100 is configured to generate and apply a neuro-stimulation signal according to a treatment regimen programmed by a physician and/or in cooperation with therapy manager 106. In one embodiment, stimulation module 104 includes a target nerve module 190 configured to track and apply the treatment parameters for a target nerve such as the hypoglossal nerve. In some embodiments, the target nerve module 190 comprises a multi-site parameter 194A, a bilateral parameter 194B, and/or a fascicle parameter 194C. The multi-site parameter 194A enables and tracks the stimulation of multiple sites (by using two or more different electrode cuffs) spaced apart along a single nerve (e.g., hypoglossal nerve) to selectively activate tongue-protruder muscles and/or tongue-retractor muscles. Accordingly the multi-site parameter 194A enables targeting multiple sites along the target nerve (including different trunks or branches) to stimulate multiple muscle groups associated with restoring airway patency.

In some embodiments, the bilateral parameter 194B enables and tracks the stimulation of a single type of nerve on different sides of the body (e.g. left side and right side) via a pair of stimulation cuff electrodes spaced apart on opposite sides of the body. In one aspect, this arrangement enables alternating activation of a particular muscle (e.g. a tongue retractor or tongue protrusor) by alternating stimulation between the left and right side of the body to reduce the duty cycle to any one nerve by 50%, which in turn, reduces any potential for nerve fatigue. In another aspect, bilateral parameter 194B enables switching to simultaneous bilateral stimulation (i.e. stimulating both nerves synchronous with a certain phase of respiration) if the patient is in a period of sleep that requires more aggressive therapy to prevent apneas.

In one embodiment, the fascicle parameter 194C enables selective stimulation and tracking of one or more different fascicles of a particular nerve being stimulated. This arrangement ensures stimulation occurs among a full range of different fascicles of a nerve, thereby potentially lessening overall fatigue of a nerve. Moreover, in some embodiments in which the nerve stimulation signal is configured to generate tone in the innervated muscle without causing a full contraction, stimulation of a fuller range of the fascicles can lead to more uniform tone throughout the muscle.

In general terms, the communication module 112 of the IPG 100 is configured to facilitate wireless communication to and from the IPG 100 in a manner familiar to those skilled in the art. Accordingly, the communication module 112 includes a reporting module 196 configured to report activities of the IPG 100 (including sensed physiologic data, stimulation history, number of apneas and/or hypopneas detected, etc.) and a programming module 198 configured to receive initial or further programming of the IPG 100 from an external source, such as a patient programmer, clinician programmer, etc.

Figure 3B:
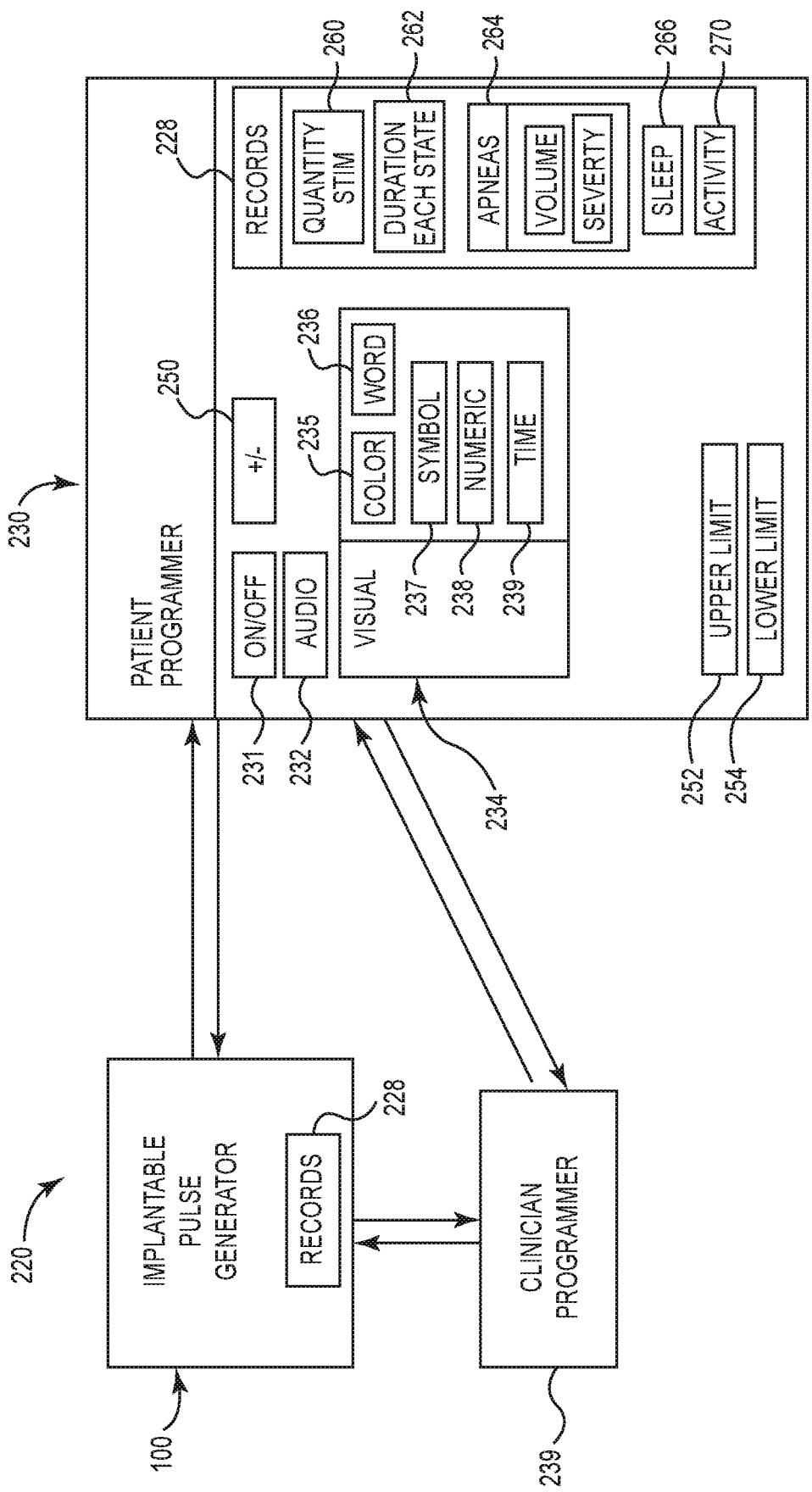
FIG. 3B is a block diagram of a therapy system including an implantable pulse generator, patient programmer, and a clinician programmer, according to an embodiment of the present disclosure.

Furthermore, in some embodiments, at periodic intervals (e.g., daily, weekly), a report is communicated to the patient. Accordingly, FIG. 3B schematically illustrates a communication system 220 including IPG 100, clinician programmer 239, and patient programmer 230. First, at these periodic intervals, a history of the therapy is stored in records 228 (i.e. a portion of memory 111) of IPG 100. At the same periodic intervals or other periodic intervals, this history is communicated to the patient programmer in a reporting format that is easily discernible by the patient.

Referring again to FIG. 3B, in some embodiments, patient programmer 230 includes an on/off function 231, an increase/decrease function 250, an audio alert function 232, and/or a visual reporting function 234. The on/off function 231 provides the patient an option to control the power state of the IPG 100 to override the automatic functioning of the therapy applied via IPG 100. Likewise, the increase/decrease function 250 enables the patient to request a preference for a higher level of therapy in the event that the patient perceives that more therapy would be helpful or a preference for a lower level of therapy in the event that that the patient is experiencing discomfort. This increase/decrease function 250 of the patient programmer 230 activates an override function 459 of an auto-titrate module 750, described in association with FIG. 9, that permits the patient to force a reduction or set an upper limit of stimulation in the otherwise automatically self-adjusting therapy. Of course, the physician is also able to limit how much control a patient is given to adjust or override their therapy.

With further reference to FIG. 3B, the audio alert function 232 provides an audio alert to the patient when attention to the patient programmer 230 or IPG 100 is warranted. Furthermore, the visual reporting function 234 is configured to communicate information about the history of therapy and/or about the state of the IPG 100 via one or more of a color light function 235, word function 236, symbol function 237, numeric function 238, and a time function 239. This information keeps the patient informed about the efficacy of the system and/or whether the system is functioning properly. For example, a green colored light in the color function 235 may indicate that the device is functioning properly while red light may indicate a malfunction. Via words and/or numerals, the patient programmer 230 also communicates details about the therapy in the last week or last day, such as the hours that stimulation was applied and how many apnea events were detected. Among other details, this information confirms to the patient that they are receiving efficacious therapy and/or can inform the patient to schedule a physician visit if the therapy is not working.

In another aspect, the history of the therapy stored in records 228 of IPG 100 is sent to the physician via a telemetry internet link for the physician to review an entire daily or weekly therapy profile. Alternatively, the physician can also download or obtain this information directly from the patient while in their office using a clinician programmer 239. This information will include the circumstances of any instances in which a patient requested changes to the therapy, such as an attempted change via the increase/decrease function 250 of the patient programmer 230. Upon review, this information (e.g., AHI data) is used by the physician to further program the IPG to be more aggressive or less aggressive as necessary by directly programming the desired therapeutic regimen and/or defining at least some of the parameters guiding an automatic self-adjusting method of therapy.

Moreover, in some embodiments, the patient programmer 230 includes an upper limit function 252 and a lower limit function 254. In one aspect, the upper limit function 252 enables a patient to set an upper limit of a therapy at which the patient is comfortable such that any increases made via the increase/decrease function 250 will be constrained by this upper limit. These limit functions 250, 252 are also controllable by a physician via communication between the clinician programmer 239 and the patient programmer 230 (or via communication directly between the clinician programmer 239 and the IPG 100). The lower limit function 254 constrains downward adjustments by the patient so that the therapy stays within a therapeutic range, and can be adjusted via the clinician programmer 239 in a manner previously described above.

In one aspect, the history communicated from the patient to the physician via records parameter 228 includes, but is not limited to, a stimulation quantity 260 and a duration spent in each of the first, second, and third states 202-206 at 262 (including parameters of the applied stimulation signal). In addition, via an apneas module 264, records parameter 228 tracks a volume, frequency, and severity of sleep disordered breathing event. Via an activity parameter 270 and sleep parameter 266, patient programmer 230 tracks activity levels of the patient (both frequency and duration of activity or sleep), as illustrated in FIG. 3B. In one aspect, this history and information is automatically formulated into graphical and numerical reports that provide the physician with a nightly synopsis of the patient's sleep apnea patterns and the effectiveness of the therapy. In addition, these reports may include a trend report within a night or for a period of multiple nights that enable detection of patterns or changes in the patient's health and/or enable evaluation of adjustments made to the therapy by the physician during the multiple night period. In some embodiments, some portion of this information available via records parameter 228 is reported to the patient.

Moreover, as later described in more detail within this disclosure, in some embodiments, the IPG 100 and system 200 is operated in second state 204 for an extended period of time (or even all night) to provide the physician with an in-home pseudo sleep study. In one aspect, the information from this pseudo sleep study is sent via a patient internet appliance to the physician to enable the physician to adjust or tailor the patient's therapy regimen.

It will be understood that the various components, functions, parameters, and modules of the systems and methods of the present disclosure can be configured, combined, and/or separated to form different groupings than those described and illustrated in FIGS. 1-10 while still achieving the general principles of the present disclosure described herein.

FIG. 4A is a schematic illustration of a system 200 for automatically treating sleep disordered breathing, according to one embodiment of the present disclosure. In one embodiment, system 200 comprises at least substantially the same features and attributes as the systems and components previously described in association with FIGS. 1-3B. As illustrated in FIG. 4A, a multi-tiered system 200 automatically initiates, terminates, and/or applies a therapy with the system operating in one of three states. Among other features, this system provides on/off control of the therapy such that the patient does not have to manually turn the IPG on or off, which insures patient compliance with the therapy while also greatly improving the patient's satisfaction and quality of life.

As illustrated in FIG. 4A, in general terms, in a first state 202 of operation of system 200, system 200 determines whether sleep-indicative behavior is present and the sensed behavior is measured against a first threshold 290 (e.g. first criteria). In some embodiments, a degree of sleep-indicative behavior is measured via a body motion/activity sensor 310 that senses body posture and "seismic" activity that is indicative of walking, body motion, talking, etc. In one embodiment, this sensor 310 comprises an accelerometer configured to sense a body position or posture. In another embodiment, the body activity sensor 310 comprises an accelerometer or piezoelectric transducer, which is configured for sensing motion. In some embodiments, sensor 310 comprises both a position-sensing component and a motion-sensing component. In one aspect, this physiologic data is tracked via body motion parameter 130 of IPG 100. It is understood that in some embodiments, the awake or sleep state of the patient is alternatively indicated or further indicated via one of more of the physiologic parameters tracked in sensing module 102 (FIG. 3A), including (but not limited to) the heart rate parameter 158 or respiratory rate parameter 159.

In either case, the IPG 100 performs this sensing of sleep-indicative behavior for a short period of time (e.g., less than 1 minute) at periodic intervals (e.g. at least every 5 minutes). If the body activity sensor 310 detects inactivity for a significant period of time (e.g. greater than 10 minutes), the system would enter a second state of operation. It is understood that each of the specific times listed above (e.g. sensing for 1 minute between intervals of 5 minutes and providing 10 minutes for an inactivity threshold, respectively) are merely examples and that other times can be selected and/or can be programmed by a physician. In some instances, a brief occasion of activity and/or cyclic periods of activity may be indicative of sleep disordered breathing behavior. Accordingly, when operating in the first state 202, the system will monitor for consistent levels of sleep-indicative behavior, such as inactivity, as well as body posture, to ensure that the system is properly identifying whether the patient is awake or asleep to thereby determine whether the system should enter the second state 202.

In some embodiments, the sensor polling times are performed on a probabilistic model in which sensing is performed according to a dynamic schedule based on the amount of body activity measured at a particular sensing time. For example, if a large amount of body activity is measured at time X, then the next polling time would take place much later at time Y. However, if a small amount of body activity is measured at time X, then the next polling time would take place at a time generally equal to (or less than) Y-X.

Figure 4B:
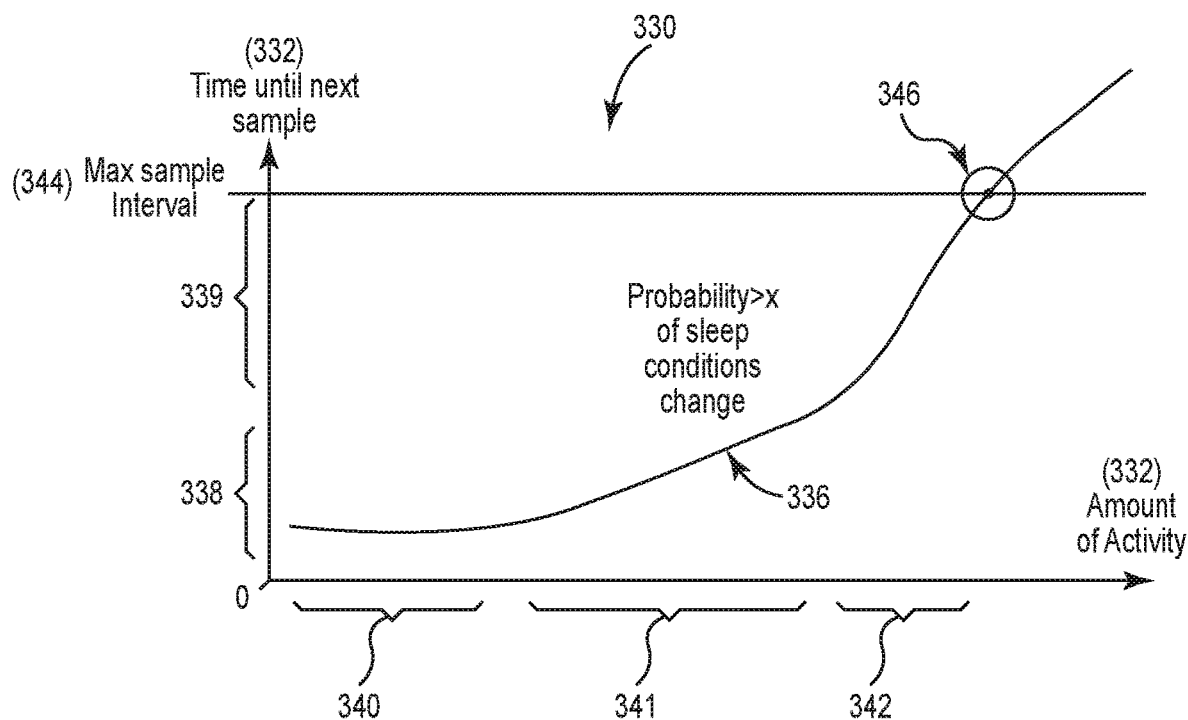
FIG. 4B is a graph schematically illustrating a probabilistic profile to determine a time interval between consecutive samples for detecting an apnea, according to an embodiment of the present disclosure.

In one non-limiting example, a probabilistic polling profile 336 (for sensing of potential apneas) is illustrated in FIG. 4B in which a magnitude of a time interval between consecutive samples 332 (y-axis) is mapped relative to an amount of sensed body activity 334 (x-axis). As previously described, the general activity level of the patient is sensed according to body motion, body posture, heart rate, respiratory rate, and/or other parameters to determine whether or not the patient is asleep or awake, or somewhere in between a sleeping state and an awake state.

As shown in FIG. 4B, according to a probabilistic sampling function, when the amount of sensed body activity is relatively low (340), then a relatively short time interval between samples (338) is applied whereas when the amount of sensed body activity is relatively high (342), then a relatively larger time interval is provided between consecutive samples (339). In general, as the amount of body activity increases, the amount of time between samples (i.e., the size of the sampling interval 332) increases until a maximum sample interval (344) is reached, at which time the size of the sampling interval remains at the maximum until the body activity level drops below the point (346) at which the maximum sample interval is initiated. Stated in other terms, this probabilistic model expresses the probability of a change in sleep conditions such that as the amount of body activity increases to a high range of body activity, there is a much lower likelihood of a change in sleep conditions because the patient is fairly active, and therefore, a much greater time interval can occur between consecutive data samples regarding potential apneic events. In general terms, this probabilistic model conserves energy, thereby contributing the longevity of the IPG 100 in the patient, among other advantages.

Referring again to FIG. 4A, in another aspect, because the body motion/activity sensor 310 (such as an accelerometer) is a low-power sensor, the first state 202 of operation minimizes current drain on the system. In other words, minimal energy is used to first determine a gross level of patient awake/activity (as compared to the activity in a sleep state) using a first level 300 of power before performing more power intensive sensing and signal processing, such as those actions that occur in the second state 202 or third state 206 of operation. In this regard, in accordance with principles of the present disclosure, in one embodiment controller 110 is configured to generate control signals to cause only the sensing module 102 (and not the stimulation module 104) to be supplied with power so that the IPG 100 conserves power until and unless sleep disordered breathing events are detected.

Moreover, in one embodiment, controller 110 can be configured to further limit the power to just one or two select sensors of the system, such as the body motion sensor (e.g., accelerometer parameter 132), so the system is not unnecessarily using power to track numerous physiologic data during periods of normal patient activity (e.g., walking, eating, working, etc.). On the other hand, in some embodiments, controller 110 can also be configured to limit power consumption by deactivating certain sensors of the system when the patient goes to sleep.

In another embodiment, controller 110 further limits power consumption by limiting the frequency at which one or more sensors capture data. For example, instead of continuously capturing data, controller 110 causes the one or more sensors to capture data once for a given time period, for example, once every 5 minutes or every 10 minutes. In yet another embodiment, to further reduce power consumption, the controller 110 causes the frequency of data capture for one set of sensors to be increased during therapy (in the third state 206) while the frequency of data capture for another set of sensors is decreased (or terminated) during therapy.

In some embodiments, first state 202 comprises an on/off function 280 including a time parameter 142. In one aspect, when operating in an "off" mode, the on/off function 280 can prevent a false transition to second state 204 by deactivating the sensing functions in first state 202 during certain periods of time (in accordance with time parameter 142), such as a standard wakefulness time period (e.g. preset nominal awake hours between 6 am and 10 pm) or other programmable waking periods. This arrangement ensures that the treatment regimen will not be active during nominal awake hours. In addition, this limit provides power conservation by preventing a transition to a higher power consumption state. On the other hand, in this embodiment, when operating in an "on" mode, the on/off function 280 enables detection of an asleep state during nominal non-waking hours (e.g., between 10 p.m. and 6 a.m.) to confirm the sleep state of the patient prior to enabling any transition to second state 204. Accordingly, upon detecting that the patient is asleep, the "on" mode permits a transition to second state 204 to detect apneas and to potentially provide a therapy in the third state 206.

In one embodiment, the on/off function 280 operates to provide an automatic nocturnal therapy function or sleep schedule parameter, in which the second state 204 of operation (and a potential implementation of the third state of operation) is automatically implemented during a standard sleeping time frame (e.g., preset nominal sleeping hours, such as but not limited to 10 p.m. to 6 a.m.).

In another embodiment, instead of operating first state 202 to trigger a transition to second state 204 based upon sensing body position/posture and sensing body motion (to determine whether the patient is awake or asleep), first state 202 is operated solely as an on/off state such that during normal waking hours (i.e., a standard wakefulness period or awake schedule), the first state 202 will not permit a transition to second state 204, thereby preventing stimulation therapy during the "off" period (i.e., during waking hours). In this embodiment, during non-waking hours (e.g., a repeating nocturnal time period, such as 10 p.m. to 6 a.m.) first state 202 becomes effectively suspended and second state 204 is automatically implemented so that the system remains in at least the second state 204 throughout the non-waking hours to check for apneas and is authorized to provide therapy as needed without spending time or energy identifying whether the patient is awake or asleep.

It will be further understood, that in some embodiments, the time function 142 is present in the second and third states 204, 206 of operation.

In one aspect of the second state 204 of the system 200, the system operates at a second level 302 of power to conserve a significant amount of power by not enabling any electrical stimulation of the target nerve. Accordingly, power is not significantly increased from the second level 302 to the third level 304 of power until the system 200 reaches the third state 206, when the patient is detected to be in a sleep state and simultaneously in a state that requires therapy to treat the apneas/hypopneas. This power savings can significantly prolong the life of the system.

In a second state 204 of operation of the system, the IPG continues to monitor the body motion/activity information, such that the system will return to the first state 202 if the sleep-indicative behavior (e.g., the patient's activity level and/or body position) fails to meet the first threshold 290, thereby indicating that the patient has entered awake or active state. In some embodiments, system 200 operates in an additive manner or progressive function such that operation in a successive state (e.g. second state 204) includes maintaining activation of or performance of the features of a previous state (e.g. first state 202) of operation.

In addition to the use of a body activity/motion sensor, in a second state 204 the IPG 100 determines whether sleep disordered breathing, such as apneas/hypopneas, are occurring via monitoring additional physiologic data. For example, the other physiologic data gathered by the IPG can be obtained through the use of one or more of a respiratory sensor, a heart rate sensor, or blood oxygen sensor (e.g. for measuring oxygen saturation), or other sensors of the type previously described in association with FIG. 3A. For example, while heart rate information can be used in a variety of ways, in some embodiments, an increased heart rate that substantially coincides with at least part of the sleep disordered breathing behavior is used to assist in confirming that the observed behavior is in fact sleep disordered breathing behavior. In particular, in one embodiment, sleep disordered breathing behavior is confirmed via detection of a decreasing heart rate generally coinciding with initiation of the sleep disordered breathing behavior and an increasing heart rate generally coinciding with the termination of the sleep disordered breathing behavior (e.g. an obstructive sleep apnea event). In another example, an identification of sleep disordered breathing behavior is corroborated by detecting a decrease in blood oxygen saturation that substantially coincides with at least part of the sleep disordered breathing behavior. In another example, confirmation of sleep disordered breathing behavior is provided via detection of hyperventilation that occurs (or is initiated) during part of the suspected sleep-disordered breathing behavior.

In some embodiments, at 324 the second state 204 operates to sample physiologic conditions (in order to detect sleep disordered breathing) in a probabilistic manner or periodically at a frequency that is inversely related to the amount or type of body activity (and posture) sensed via sensor 310, in a manner consistent with that previously described in association with FIG. 4B.

In one embodiment, as illustrated in FIG. 4A, the primary physiologic data used to determine whether or not an apnea is occurring includes a bio-impedance signal 312 (e.g., a trans-thoracic parameter or a non-thoracic parameter) and/or a respiratory pressure signal 314 (e.g., intrapleural or other respiratory parameter), as further described later in more detail in association with FIGS. 5-7. In the event that apneas or hypopneas suitable for treatment are detected, the system transitions from the second state 204 to the third state 206. In some embodiments, system 200 operates via a bypass function in which second state 204 is omitted thereby enabling the system 200 to operate in an acute mode. In this arrangement, as soon as a patient's patient sleep is detected in first state 202 (or the "on" function is activated), system 200 automatically proceeds to implementing therapy in the third state 206. In one non-limiting example, this arrangement is employed when a patient has an acute case of sleep disordered breathing (e.g., obstructive sleep apnea, hypopneas, etc.) such that any time the patient enters a sleep state, it is practically assured that sleep disordered breathing will take place. Moreover, a physician can program system 200 to operate in an acute mode as patient circumstances warrant. In a third state 206 of operation of the system 200, the system 200 applies a therapy to treat sleep disordered breathing, such as the use of stimulation of the hypoglossal nerve (as represented by output 320 in FIG. 4A) synchronous with inspiration to keep the upper airway from obstructing. In some embodiments, stimulation of the hypoglossal nerve is synchronized to be OFF during at least a portion of expiration. In some embodiments, the therapy is applied via an auto-titrate module 750 as will be further described in association with FIG. 9.

In this third state 206, the system 200 will periodically or temporarily suspend therapy at regular intervals (for example, every 5, 10, or 15 minutes) for a period of time (e.g., 30 seconds, 1, 2, 3, 4, 5 or more minutes) to determine whether or not apneas/hypopneas are occurring or whether an apnea severity score is above a predetermined threshold. In other words, system 200 is programmable to vary the amount of time that a stimulation protocol is suspended and to vary the frequency at which a stimulation protocol is suspended.

Figure 4C:
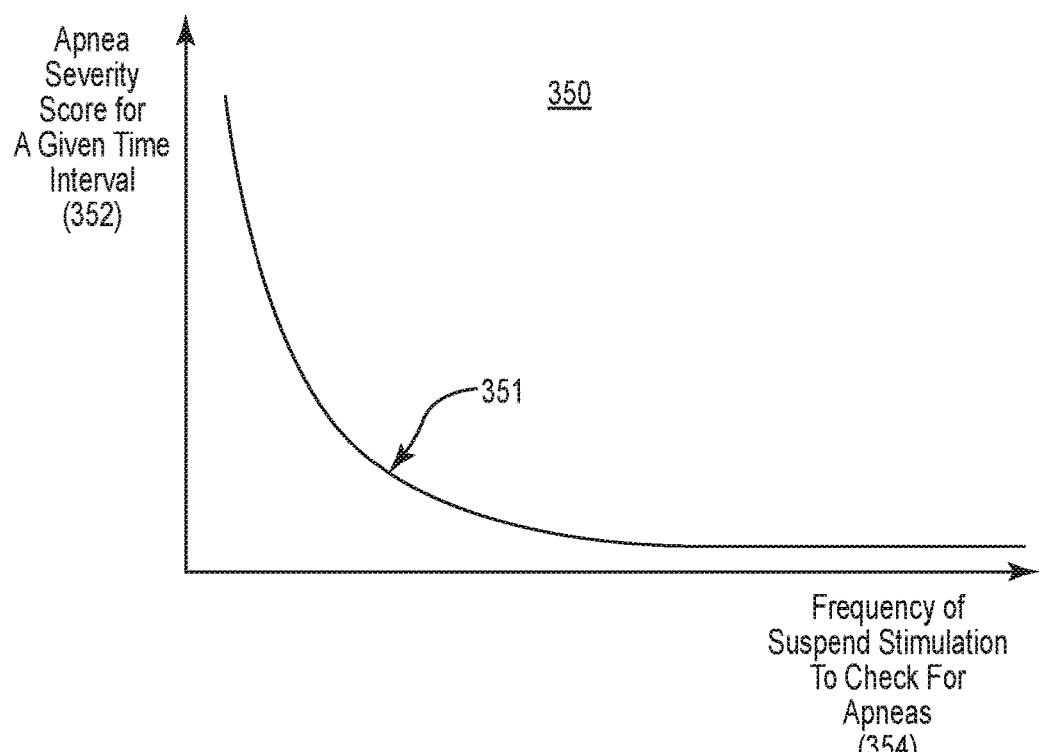
FIG. 4C is a graph schematically illustrating a probabilistic profile to determine a frequency at which stimulation will be suspended in order to detect apneas, according to an embodiment of the present disclosure.

In some embodiments, the frequency of suspending stimulation is based on a probabilistic profile 351 as schematically illustrated by graph 350 in FIG. 4C. According to this profile 351, the greater the apnea severity score (based on at least a frequency and/or intensity of apneas), the less often that therapy will be suspended to check for apneas. On the other hand, when there is a lower apnea severity score, the more often that therapy will be suspended as fewer adjustments are expected to be made. In addition, in the latter scenario, the time of suspension can be longer as it is expected that less therapy is needed. Of course, in some embodiments, the system 200 is also programmable to have longer or shorter durations of suspended therapy independent of the frequency at which therapy is suspended.

In some embodiments, additional parameters are considered in determining the duration or, or the frequency of, suspending therapy to check for apneas. For example, one parameter is how long sleep has been going on because too frequent or too long of a suspension of therapy early in the intended sleep period (e.g., the first hour) could inhibit the patient from getting to sleep. As another example, if other samples (in the early periods of the intended sleep period) have indicated a high apnea severity score requiring significant stimulation therapy, then another sample may not be needed for some time or even all night. On the other hand, if apnea severity scores early in the intended sleep period were low, then a longer suspension period may be needed to get a statistically significant respiration cycles. These determinations also can be linked to other sleep data. For example, if a body-motion sensor or body-position sensor indicates less restful sleep, then suspension should probably occur less frequently and for less time.

A temporary suspension of the therapy reverts the system 200 to operation in the second state 204 in which the IPG 100 monitors physiologic data for detection of apneas and/or hypopneas without applying a therapy. If no apneas/hypopneas are detected during this temporary suspension of therapy (or if the apnea severity score is below the predetermined threshold), the IPG 100 will remain in the second state 202 of operation. On the other hand, if apneas or hypopneas are still detected (or the apnea severity score is above the predetermined threshold) during a temporary suspension of therapy, the system will once again resume operation in the third state 206 in order to deliver the needed stimulation therapy for treating the sleep disordered breathing behavior.

Figure 4D:
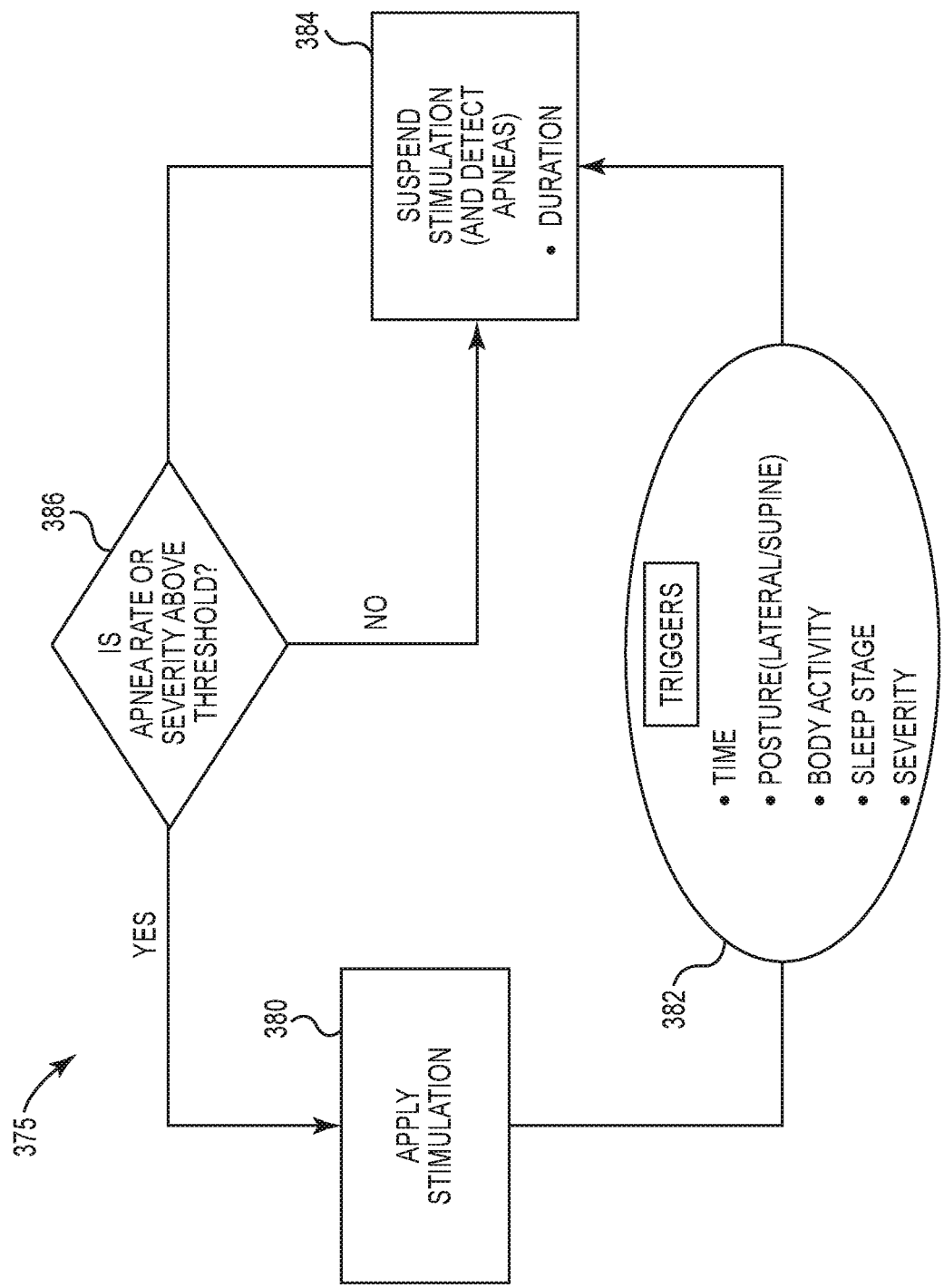
FIG. 4D is a block flow diagram schematically illustrating a method of suspending stimulation in order to detect apneas, according to an embodiment of the present disclosure.

While the automated decision by system 200 to suspend therapy can be based strictly on time parameters and/or a time-based probabilistic profile as previously described, in other embodiments the automated decision by system 200 to suspend therapy is made by additional factors independent of, or in combination with, time-based parameters. With this in mind, FIG. 4D schematically illustrates a method of initiating and terminating suspension of therapy as performed as part of third state 206 (or as part of a state-less decision model). FIG. 4D illustrates a loop 375 in which stimulation is applied (380) until or unless one or more triggers 382 are present, at which time a suspension function causes system 200 to move to a state of suspended therapy (at 384). One of these triggers 382 includes a preset time-based model, such as the probabilistic model previously described in association with FIG. 4C or a fixed time interval. In some embodiments, a posture change function provides another trigger to temporarily suspend application of a stimulation signal based on a change in posture, such as a change in sleeping position when the patient rolls over between a supine and lateral position. In one example, such body position would be monitored by the position-sensing component 132 of body parameter 130 in sensing module 102 of implantable pulse generator 100, as illustrated in FIG. 3A. These changes in position can interrupt an apneic state, and therefore such repositioning is an appropriate trigger to suspend therapy to enable detection of whether any apneas are occurring so that therapy is not unnecessarily applied when the changed sleeping position terminated the apnea(s).

Moreover, even when a therapeutic nerve stimulation signal is not being applied when a patient in the supine position, in some embodiments, the sensed supine position is used to as a trigger to check for sleep-disordered breathing behavior more frequently (for example in the second state 204 in FIG. 4A) because patients are generally more prone to exhibit sleep disordered breathing behavior in the supine position. Similarly, when other physiologic data such as respiratory waveforms, bio-impedance, heart rate, blood oxygen saturation etc. indicate that sleep disordered breathing behavior is occurring, knowing whether the patient is in the supine position or not helps to confirm whether or not the suspected sleep disordered breathing behavior is truly sleep disordered breathing behavior, as described herein in more detail in association with at least parameter 130 of FIG. 3A, second state 204 in FIG. 4A, and/or parameter 423 in FIG. 4F.

For example, if the monitored physiologic data in cooperation with the body position data reveals that a particular patient rarely exhibits sleep disordered breathing behavior when in a lateral decubitis (i.e., lying on their side), then this body sensing information helps to prevent false positives of sleep disordered breathing behavior when the patient in lying on their side. Alternatively, this same data would ensure the accuracy of indicating sleep disordered breathing behavior when the conclusion from primary physiologic data indicating sleep disordered breathing behavior is bolstered by sensing the patient is in a supine position, where most (if not all) of their sleep disordered breathing behavior takes place.

In yet other embodiments, the body position data is used as part of method to determine the aggressiveness of a therapy regimen to apply to the patient. For example, in one embodiment, when the body position parameter 132 reveals that the patient is in a supine position they will receive (via a therapy manager 106 of IPG 100 in FIG. 3A and auto-titrate module 750 in FIG. 9) a first regimen of therapy and when in a lateral decubitis position (laying on their side), they will receive a second regimen of therapy that is less aggressive than the first regimen of therapy. However, for other patients, the body position data (via parameter 132) is used to apply a less aggressive therapy when the patient is in a supine position and a more aggressive therapy when the patient is in a lateral decubitis position.

Another trigger also includes body activity, as a patient may get out of bed for a period of time, thereby terminating apneic events.

In some embodiments, a severity score of the sleep disordered breathing behavior acts as a trigger (382) to suspend stimulation in order to detect or monitor for sleep disordered breathing behavior. For example, in one embodiment, a frequency of suspending stimulation (to monitor for sleep disordered breathing) is inversely proportional to the severity score of the sleep disordered breathing behavior. In other words, the more severe (e.g. frequency, duration, intensity) the sleep disordered breathing behavior, the less often that stimulation is suspended to check for such breathing behavior and the less severe the sleep disordered breathing behavior, the more often that stimulation is suspended to check for disordered breathing behaviors.

In some embodiments, one or more different stages of sleep may act as triggers to warrant suspending therapy to check whether or not any sleep disordered breathings behavior is occurring. For example, if the sensed physiologic parameters reveal that the patient is likely in a deeper stage of sleep for a sufficient period of time, then these sleep stages would trigger the suspension of therapy to move the system 200 out of the stimulation mode and start detecting possible sleep disordered breathing. Accordingly, in some embodiments, as described later in more detail, system 200 is trained by operating simultaneously with a sleep study (e.g., polysomnography) in which different sleep stages (among other patterns) are recognized and in which a patient's different physiologic parameters are tracked relative to those sleep stages. By correlating these sleep study parameters with sensed physiologic parameters of the IPG 100 (FIG. 3A), the IPG 100 becomes calibrated for a particular patient to recognize sleep stages and other sleep patterns which are useful in some embodiments for applying and/or suspending therapy via the IPG 100.

With further reference to FIG. 4D, a suspension of therapy is terminated and therapy is resumed via reversion to third state 206 according to one or more triggers 382 such as a preset (or probabilistic) time interval or when an apnea severity score detected during the suspended therapy rises above a threshold (e.g., an AHI of 10). It will be understood that in this context the term apnea is used to refer generally to obstructive sleep apnea, hypopneas, or central sleep apnea. Therapy is then applied until one of the triggers 382 forces suspension of therapy.

In general terms, this arrangement insures that therapy is suspended when it is no longer necessary and resumed when necessary. This suspension mechanism aids in preventing overstimulation/fatigue of a nerve, conserves power, and reduces patient annoyance due to stimulation therapy that occurs when the patient is not sleeping.

In some embodiments, this multi-tier system 200 illustrated in at least FIG. 4A operates according to a progressive function that provides a dynamic or progressive activation of successive states of operation along with a reversion function in which the system 200 automatically reverts to one of the lower states of operation when operation in a higher state becomes unnecessary. In one aspect, the first and second state employ a sensing portion of the IPG 100 without activation of the stimulation portion of the IPG 100. This arrangement saves power in cooperation with power management module 108 (FIG. 3A), which can increase the longevity of an implantable battery-operated device, such as the IPG 100. Moreover, because the first state of operation employs only a single sensing parameter (e.g. the body motion/activity sensing) in some embodiments, the IPG 100 can operate in a very low state of power most of the time. In addition to conserving power as part of the power management function of module 108, this arrangement minimizes patient annoyance by insuring that therapy is provided only when needed. Even when criteria to move from the first state 202 to the second state 204 of operation are met, a relatively low state of power is employed in a second state 204 of operation while sensing appropriate physiological sensors to detect sleep disordered breathing behavior. Moreover, this relatively low state of power in the second state 204 of operation is substantially less (for example, less by at least an order of magnitude) than the amount of power used in a third state 206 of operation to provide therapy via stimulating a target nerve.

In another aspect, in addition to conserving power, limiting the first state 202 or second state 204 of operation to a low power state in which no stimulation takes place when not affirmatively providing a neuro-stimulation therapy (such as in the third state 206) also can avoid an unnecessary long term stimulation of the nerve.

Accordingly, a multi-tier system 200 in accordance with principles of the present disclosure ensures that the patient will automatically receive therapeutic treatment for their sleep disordered breathing behaviors at the appropriate time without undue interference with, or fatigue of, normal nerve function while the system 200 dynamically manages power consumption and operational states of the IPG 100.

It is also understood that the system 200 of providing therapy can also be provided via protocols other than the state-based protocol illustrated and described in association with FIG. 3A. For example, in other embodiments, system 200 is implemented via rule based protocols and/or other protocols that do not strictly rely on the sequence and/or interaction of three states of operation.

It is also understood that the identification of a sleep apnea or hypopnea via an IPG 100 and the associated systems and methods described herein is performed in a manner that varies somewhat from how apneas/hypopneas are identified in a sleep study. For example, in a sleep study, an apnea or hypopneas is defined as a certain physiologic events, such as a decrease (e.g., 3%) in blood oxygen saturation for a period of at least ten seconds. Moreover, in a sleep lab, the physician scores events using predefined criteria, based on the sensor parameters obtained in a sleep lab, and this scoring results in the AHI count.

Accordingly, because the implantable systems described herein do not have sensors that correspond exactly with the types of sensors used in a sleep lab, the AHI count determined via the implantable systems in accordance with embodiments of the present disclosure will differ somewhat from the sleep lab-determined AHI count. Nevertheless, the implantable system/methods of embodiments of the present disclosure include a number of physiologically sensed data (e.g., internally measured blood oxygen saturation) that can act as surrogates for the types of information obtained in a sleep lab (e.g., externally measured blood oxygen saturation).

Figure 4E:
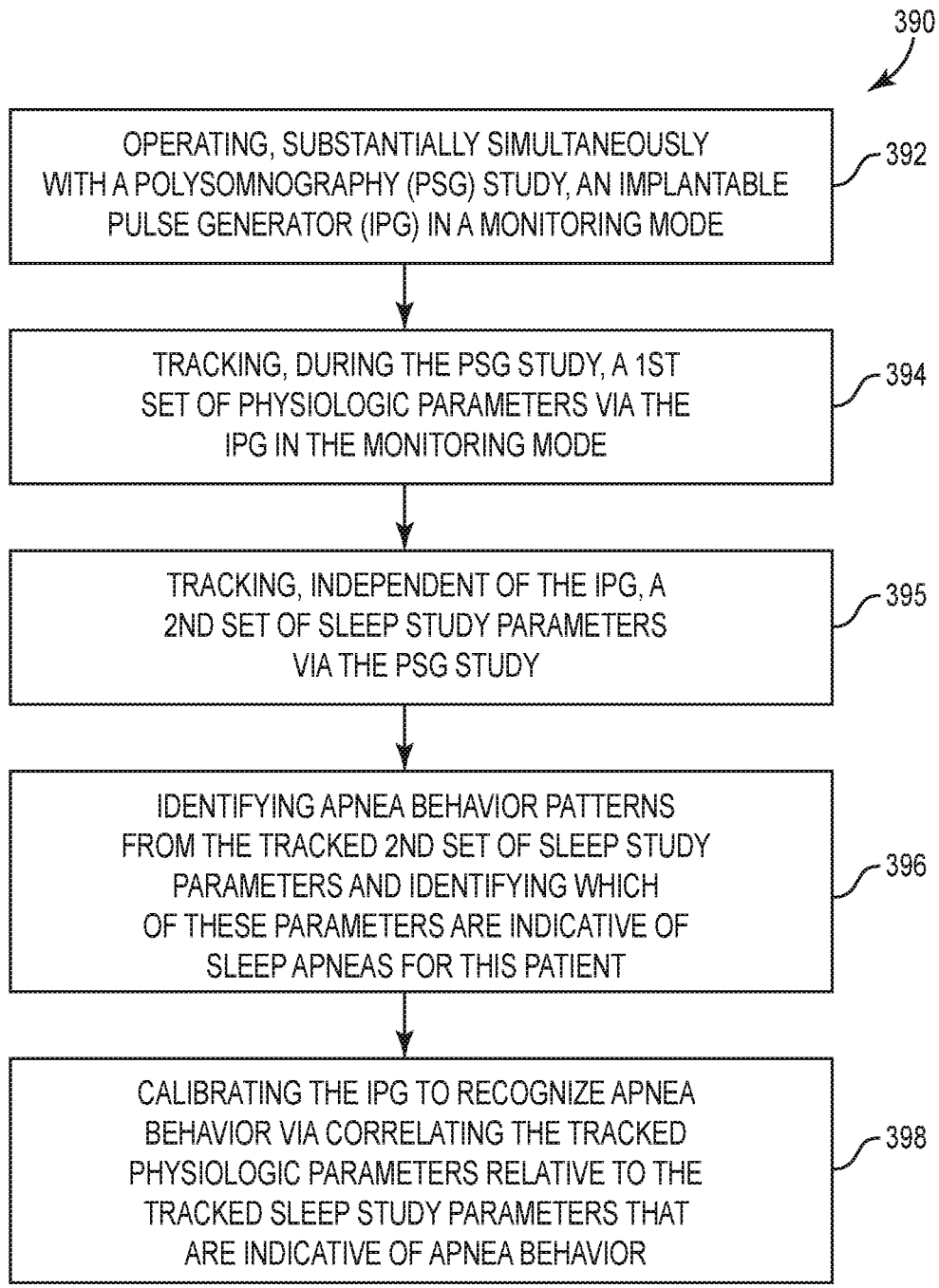
FIG. 4E is a flow diagram schematically illustrating a method of correlating sleep study parameters and therapy parameters associated with an implantable pulse generator, according to an embodiment of the present disclosure.

FIG. 4E is a flow diagram that schematically illustrates a method 390 of correlating sleep study parameters with physiologic parameters of the implantable pulse generator system, in accordance with an embodiment of the present disclosure. As illustrated in FIG. 4E, at 392 the method 390 includes operating, substantially simultaneously with a polysomnography (PSG) study, an implantable pulse generator (IPG) system in a monitoring mode. At 394, a first set of physiologic parameters is tracked, during the polysomnography study, via the IPG system in its monitoring mode. A second set of sleep study parameters is tracked, independent of the IPG system, via the polysomnography study (at 395). At 396, method 390 includes identifying sleep disordered breathing patterns (e.g. apneas and/or hypopneas) from the tracked second set of sleep study parameters and identifying which of these parameters are indicative of sleep disordered breathing for a particular patient. At 398, the implantable pulse generator is calibrated to recognize sleep disordered breathing for a particular patient via correlating the tracked physiologic IPG-based parameters/conditions relative to the tracked PSG-based sleep study parameters that are indicative of sleep disordered breathing behavior for that particular patient.

With this in mind, FIG. 4F provides a chart 400 that schematically illustrates a comparison of some sleep study parameters 402 relative to some IPG therapy parameters 408. As previously noted, in some embodiments, the IPG therapy parameters 408 are calibrated relative to one or more related sleep study parameters 402. For example, an IPG 100 within a patient operates during a sleep study such that parameters for the IPG 100 and parameters for the polysomnograph (PSG) monitor are both tracked. By looking at profiles of sleep disordered breathing behavior, a correlation is made between the IPG parameters 418 and the PSG parameters 402 such that the IPG 100 is calibrated to sleep study data.

In one example, one sleep study parameter includes an airflow measured at the mouth-nostril airflow pathway (410), which is indicative of a sleep disordered breathing when this airflow is substantially reduced. In one aspect, the mouth-nostril airflow is measured at the nostrils and/or mouth. While this parameter may not be exactly reproduced in embodiments which are totally implantable, a combination of parameters to be described in more detail in association with FIGS. 5-7B provides a good indication of an sleep disordered breathing behavior that is commensurate with the extent to which the mouth-nostril-airflow parameter 410 of a sleep study indicates sleep disordered breathing. In particular, a dramatic change in the amplitude patterns 416 (and in opposite directions) of both a bio-impedance signal and a respiratory pressure signal provide an indication that a sleep disordered breathing behavior (e.g., an apneic event) 413 is occurring or has occurred. Accordingly, this combination of the amplitude patterns 416 of the bio-impedance and respiratory pressure signals (determined via IPG 100 and system 100) act as a surrogate to the mouth-nostril-airflow parameter 410 typically measured in a sleep study.

In another example, referring again to FIG. 4F, the internally measured blood oxygen saturation parameter 417 (via IPG 100 and system 200) acts as a surrogate for the externally measured blood oxygen saturation parameter 411 available via a sleep study. While there are some differences between these two respective parameters 417 and 411, by training IPG 100 via a sleep study, the internally measured blood oxygen saturation parameter 417 (via IPG 100 and system 200) will be calibrated relative to the externally measured blood oxygen saturation parameter 411 to account for such differences. In this way, the internally measured blood oxygen saturation parameter 417 can function as an accurate trigger for occurrences of sleep disordered breathing in this patient.

In other respects, the one or more physiologic data points of the implantable systems/method of the present disclosure may provide information that is more helpful in determining an automatic self-adjusting therapy than information obtained via a sleep lab. For example, embodiments of the present disclosure measure intra-pleural pressures 418, which can be correlated to the degree of obstruction of the upper airway. As the obstruction increases in a progression from an open airway to hypopnea to a full obstruction, the magnitude of the intra-pleural pressure increases. Accordingly, embodiments of the present disclosure enable measurement and identification of increases in the intra-pleural pressures 418 which in turn, are indicative of sleep disordered breathing events 415. In one aspect, this feature enables the systems/methods of present disclosure to provide sleep disordered breathing scoring (e.g., apnea scoring) that is more sophisticated than conventional scoring methods associated with a sleep lab.

Moreover, in one embodiment, after initially calibrating the IPG 100 during a sleep study, the IPG 100 is permitted to operate during a second sleep study so that the IPG 100 is able to self-learn in direct association with the data provided via the PSG. Using this method, physiologic data sensed via the IPG 100 that is indicative of an sleep disordered breathing behavior is matched with indicative physiologic data/observations sensed via the PSG monitoring system that is indicative of sleep disordered breathing behavior. In one aspect, this direct calibration lessens the time that the IPG would spend self-learning an appropriate baseline therapy regimen for a patient because the PSG would allow direct real-time programming of the IPG as the sleep study occurs. In other words, the IPG would be automatically programmed with a pattern of the sleep disordered breathing patterns, sleep habits, etc. so that the IPG will know in advance for this patient which time of night, day of the week, body position, heart rate, etc. that will trigger apneic behavior or normal breathing. As a result, the automatic therapy regimen will be tailored to a specific patient's needs rather than having the patient receive a conventional one-size-fits-all stimulation therapy that would have a greater potential to consistently overstimulate or understimulate the patient.

In this regard, FIG. 4F further illustrates such additional parameters which are correlated with the PSG-related primary parameters and the IPG-related primary parameters. In some instances, these additional parameters may or may not be tracked in a polysomnography study or via the IPG. As shown in FIG. 4F, a night-of-week parameter 420 tracks which night or nights of the week that the sleep disordered breathing behavior occurs while time-of-day parameter 421 tracks one or more points in time within a 24 hour period that the sleep disordered breathing occurs. A sleep stage parameter 421 tracks which, and how many, stages of sleep within a sleeping period (such as 10 pm to 6 am) that the sleep disordered breathing occurs. A body posture parameter 423 tracks which body posture coincides with occurrence of the sleep disordered breathing, and when (relative to a sleep stage, time of day, or night-of-the-week) the patient typically enters that body posture. Other parameters, such as patient demographic factors 424 are tracked as well, such as age, sex, smoker, weight, neck, hypertension, etc.

In some embodiments, this method of correlation includes correlating a sleep stage parameter 425 relative to sleep disordered breathing events and relative to an array of IPG-related parameters 426, such as a heart rate, a blood oxygen saturation, a bio-impedance, and/or a respiratory pressure.

Figures 4G, 4H:
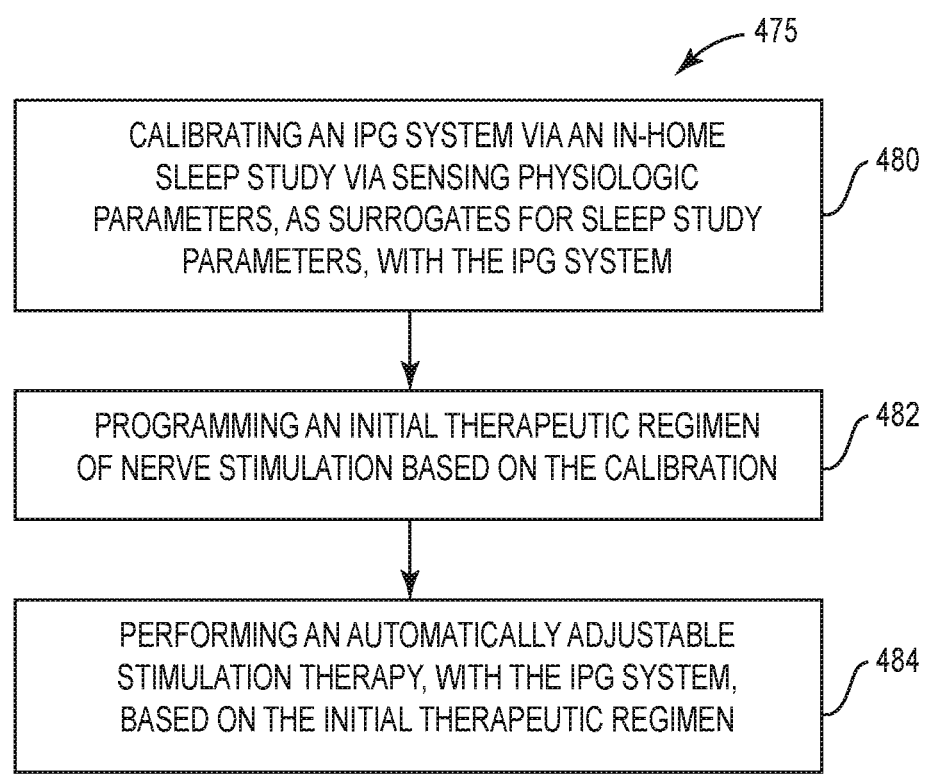
FIG. 4G is a chart schematically illustrating an index for implantable pulse generators, according to an embodiment of the present disclosure.
FIG. 4H is a flow diagram schematically illustrating a method of therapy based on an implantable pulse generator system calibrated relative to a sleep study, according to an embodiment of the present disclosure.

In another embodiment, as illustrated by chart 450 of FIG. 4G, after a number of IPG-based systems 456 (e.g., IPG 1, IPG 2, etc.) are calibrated relative to sleep study parameters 454 (e.g. PSG 1, PSG 2, etc.) for a number of patients 452 (e.g. Joe, Fred, etc), embodiments of the present disclosure can use a correlation of the sleep study parameters relative to the IPG parameters to develop a predictive index 460 (e.g., responsive ratings) that would predict how beneficial an IPG might be for a particular patient prior to implantation of the IPG in the patient. In one aspect, the responsive rating expresses on a scale from 1 to 10 (with ten being the highest) how efficacious the implantable pulse generator would be to treat sleep disordered breathing for a patient having the type of polysomnography study and demographics like those provided in the chart.

In some embodiments, in addition to or instead of sensing physiologic parameters via IPG 100 during a formal sleep study, system 200 (FIG. 4A) of an implanted IPG 100 is operated only in the second state 204 for an extended period of time (or even all night) to provide the physician with a pseudo sleep study performed in the home of the patient. In other words, the IPG 100 and system 200 act as an implanted polysomnography device. In one aspect, the data from the in-home pseudo sleep study is sent via a patient internet appliance (e.g., patient programmer 230 of FIG. 3B) to the physician, thereby allowing the physician to better tailor the stimulation therapy to the sleeping habits/behavior of the patient. In some respects, the in-home pseudo sleep study can potentially provide better data than a formal sleep study regarding the actual sleeping behavior or habits of the patient because the patient would be sleeping in their normal sleeping environment, such as their own bed, under their own climate control, etc.

Accordingly, FIG. 4H illustrates one embodiment of a method 475 of treating sleep disordered breathing, according to an embodiment of the present disclosure. As illustrated in FIG. 4H, at 480 method 475 includes calibrating an IPG system via an in-home pseudo sleep study via sensing physiologic parameters, as surrogates for conventional sleep study parameters, with the IPG system. At 482, in initial therapeutic regimen of nerve stimulation therapy, based on the calibration, is programmed into the IPG system. At 484, method 475 includes performing an automatically adjustable stimulation therapy, via the programmed, calibrated IPG system, based on the initial therapeutic regimen.

In some embodiments, prior to performing the in-home pseudo sleep study, sensing parameters of the IPG 100 and system 200 are calibrated relative to conventional sensing parameters of a formal sleep study by operating the IPG 100 and system 200 in a sensing mode (e.g. second state 204 in FIG. 4A) during the formal sleep study in a manner substantially the same as described above.

While any number of physiologic parameters can be used with varying success to detect sleep disordered breathing, such as an apnea and/or hypopnea, in one embodiment of the present disclosure, the sensing module 102 of the IPG 100 detects apneas/hypopneas via a trans-thoracic bio-impedance parameter. In particular, a measurement of trans-thoracic impedance is used to track the relative amplitude of the respiratory waveform. Physiologically speaking, the bio-impedance of the lungs varies as the lungs fill and empty with air. An air filled lung has a slightly higher impedance. In another aspect, a varying respiratory drive will also cause the amplitude of the bio-impedance to vary, with a larger respiratory drive increasing the signal amplitude of the bio-impedance.

Upon obtaining the trans-thoracic bio-impedance signal via the sensing module 102 of IPG 100, the bio-impedance signal is further processed to identify an average peak amplitude over time. A sleep disordered breathing event is detected by further identifying cyclic amplitude variations that occur for a duration substantially similar to the already known duration of a typical apneic event. In this regard, FIG. 5 provides a graph 500 schematically illustrating a respiratory airflow signal 502 corresponding generally to respiratory drive/effort and a trans-thoracic, bio-impedance signal 504. As shown in FIG. 5, a relative amplitude (represented by y-axis 508) of these signals is separately tracked over a time period (represented by x-axis 506).

In the above-described embodiment, the bio-impedance signal 504 is obtained via a trans-thoracic sensing mechanism. However, in other embodiments, the bio-impedance signal 504 is obtained via other sensing mechanisms such as previously identified in association with bilateral nerve electrode parameter 148 of FIG. 3A. For example, in one embodiment, when a stimulation cuff electrode is provided on each of the left and right sides of the body to enable potential bilateral stimulation (simultaneous or alternating), a bio-impedance can be measured between these respective nerve electrode cuffs, which are spaced apart on opposite sides of the body. In the event of a collapsed airway, a change in the pattern of this bio-impedance signal will be detected and can be used to indicate an apneic/hypopnea event. Of course, monitoring a bio-impedance signal in embodiments of the present disclosure is not strictly limited to either the trans-thoracic sensing mechanism or the sensing mechanism provided by the spaced apart stimulation cuffs.

In particular, in observing the amplitude signal (of the bio-impedance measurement) during a typical apneic event, the system would observe a 10 to 40 second time period of a low amplitude signal (which directly corresponds to the obstruction) followed by a very high amplitude signal (of the bio-impedance measurement) due to the arousal from sleep and the ensuing hyperventilation. In FIG. 5, the bio-impedance signal 504 during normal respiration is represented by segment 540, while the relatively low amplitude bio-impedance signal 504 during the sleep disordered breathing event is represented by segment 542 which is then followed by the relatively high amplitude signal in high-effort segment 544. Moreover, the relatively low amplitude segment 542 of the bio-impedance signal 504 substantially corresponds to the relatively low amplitude segment 532 of the airflow signal 502 caused by the obstruction. Finally, the high amplitude segment 534 of airflow signal 502 represents an increase to respiratory drive as the patient is aroused and exerts a high effort (represented by portion 274) to recover from the sleep disordered breathing event(s).

Figure 5:
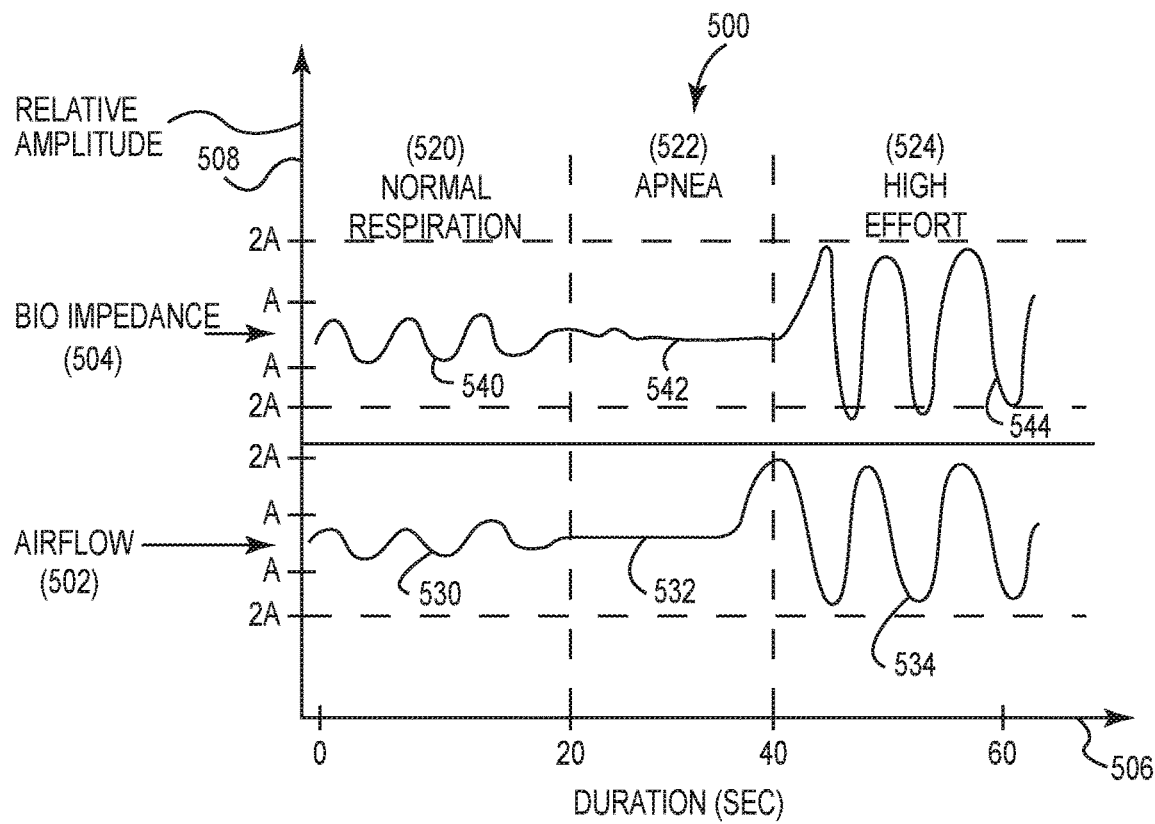
FIG. 5 is a graph array schematically illustrating detection of an apnea via a bio-impedance signal, according to an embodiment of the present disclosure.

Accordingly, in one embodiment the IPG 100 uses this physiologic data illustrated in FIG. 5 to identify a sleep disordered breathing behavior. In one aspect, this data would be detected via a sensing module 102 of IPG 100 with system 200 in a second state 204 of operation.

In another embodiment of the present disclosure, the sensing module 102 of IPG 100 detects an apnea or hypopnea via a respiratory pressure parameter. As previously described in association with FIGS. 1-2, a measurement of respiratory pressure can be made by placing a pressure sensor in the extrapleural space (represented by 89 in FIG. 2) or the intrapleural space (represented by dashed lines 88 and identifier 90 in FIG. 2). The respiratory pressure signal will provide a respiratory signal proportional to the negative pressures generated during inspiration. For example, the magnitude of the amplitude of the respiratory pressure will vary due to the level of respiratory drive or effort and also will vary based on any flow restriction in the upper airway.

Figure 6:
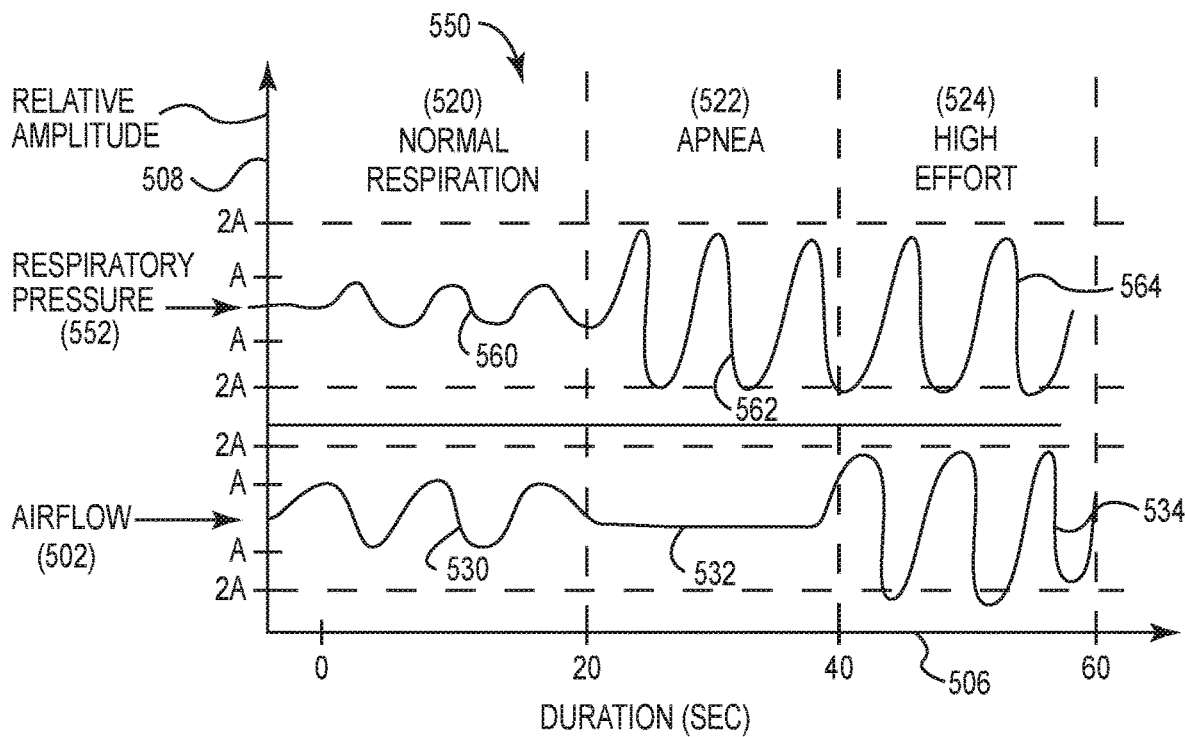
FIG. 6 is a graph array schematically illustrating detection of an apnea via an respiratory pressure signal, according to an embodiment of the present disclosure.

In this regard, FIG. 6 provides a graph 550 schematically illustrating the respiratory airflow signal 502 corresponding generally to respiratory drive/effort and a respiratory pressure signal 552. As shown in FIG. 6, a relative amplitude (represented by y-axis 508) of these signals is separately tracked over a time period (represented by x-axis 506).

In particular, in observing the amplitude signal (of the respiratory pressure measurement) during a typical apneic event, the system would observe a 10 to 40 second time period of a high amplitude signal (which directly corresponds to the obstruction) continued by a very high amplitude signal (of the respiratory pressure measurement) due to the arousal from sleep and the ensuing hyperventilation. In FIG. 6, the respiratory pressure signal 552 during normal respiration is represented by segment 560, while the relatively high amplitude respiratory pressure signal 552 during the sleep disordered breathing event is represented by segment 562 which is then followed by the relatively high amplitude signal in high-effort segment 564. Moreover, the relatively high amplitude segment 562 of the respiratory pressure signal 552 (representing an increased magnitude of inspiratory negative pressure) substantially corresponds to the relatively low amplitude segment 532 of the airflow signal 502 caused by the obstruction.

Thus, the sensing module 102 of the IPG 100 (when operating in second state 204 of multi-tier system 200) can detect apneas or hypopneas (using physiologic data such as that illustrated in FIG. 6) by tracking the respiratory amplitude from a respiratory pressure sensor and identifying average peak pressures and detecting cyclic amplitude variations that have a time component similar to the period of apneic events.

Figure 7A:
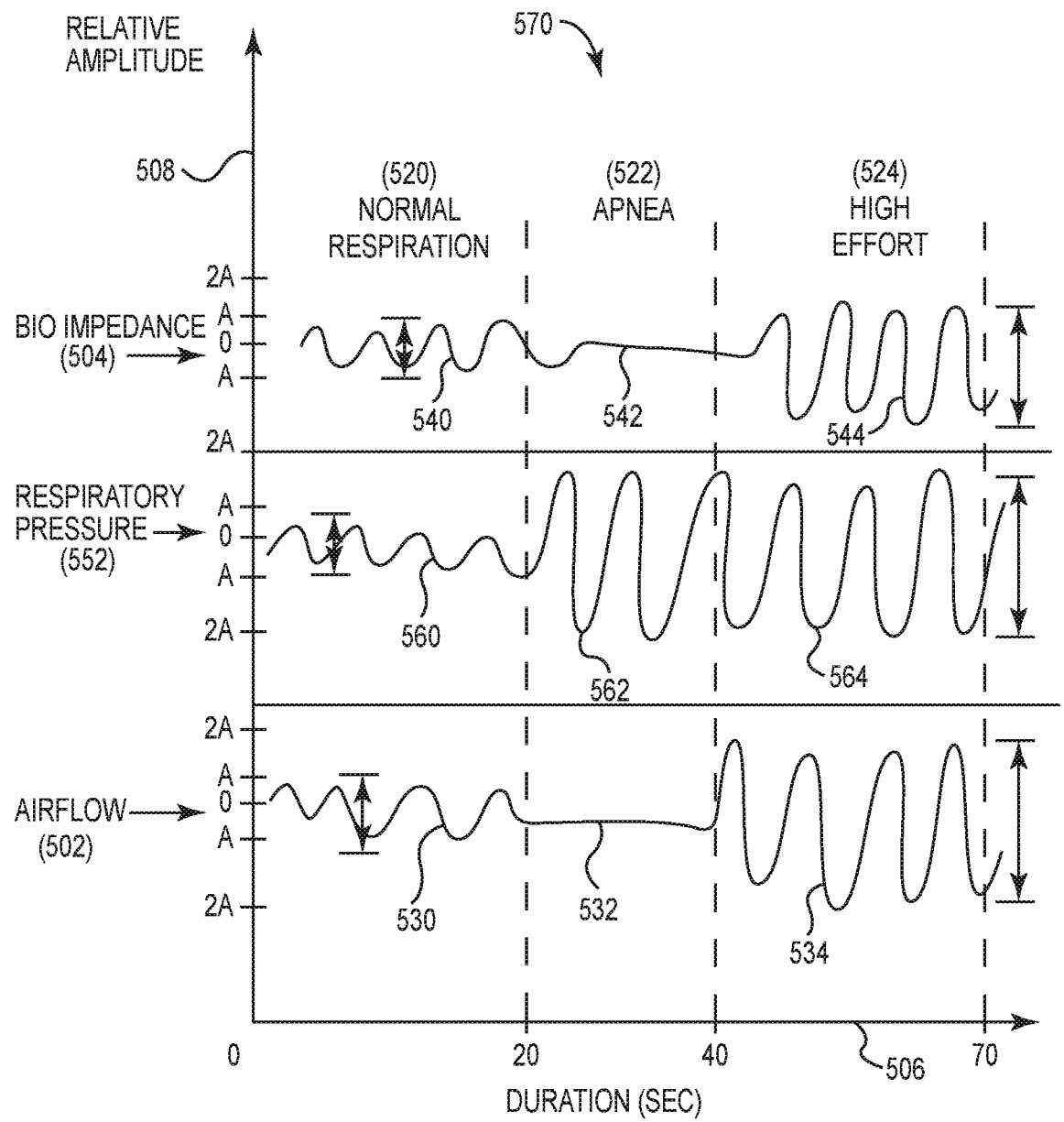
FIG. 7A is a graph array schematically illustrating detection of an apnea via mapping a bio-impedance signal and a respiratory pressure signal, according to an embodiment of the present disclosure.

In yet another embodiment, sensing module 102 of IPG 100 can detect an apnea or a hypopnea by using more than one primary physiologic signal as a determining factor. Accordingly, as illustrated in FIG. 7A, both a bio-impedance signal 504 and a respiratory pressure signal 552 are used together to determine when an apnea or hypopnea is occurring. While the example shown in the FIG. 7A illustrates a trans-thoracic bio-impedance signal, it is understood that other bio-impedance signals can be tracked and used in combination with a respiratory pressure signal 552 to determine whether an apnea or hypopnea is occurring.

While using either a bio-impedance sensing signal 504 (FIG. 5) or a respiratory pressure sensing signal 552 (FIG. 6) alone will provide some level of apnea detection, these respective sensing signals lack specificity as the signal amplitudes both vary with respiratory drive and with restricted/obstructed airflow (apnea/hypopnea). However, the combination of using physiologic data from both a bio-impedance sensor and a respiratory pressure sensor provides excellent apnea/hypopnea detection as both sensors have significant changes in amplitude due to increased respiratory drive. In some embodiments, these substantial changes comprise opposing amplitude changes during the occurrence of the apneas/hypopneas. In particular, as illustrated in FIG. 7A, the respiratory pressure amplitude (signal 552) significantly increases (segment 562) due to the flow restriction and the bio-impedance signal (504) decreases (segment 542) to a negligible level in response to the flow restriction (segment 532) of airflow signal 502. As illustrated by the sleep disordered breathing 522 portion of graph 570 of FIG. 7A, when the relative amplitudes of the two signals 504, 552 move in opposite directions (one increasing by large amounts and one decreasing by large amounts) as depicted in the sleep disordered breathing portion 522 of graph 570, then an obstructed air flow or apnea/hypopnea is detected. However, it will be understood that in some embodiments, because of variations from patient to patient, the respiratory pressure can decrease (instead of increasing) during at least part of the sleep disordered breathing behavior. To the extent that actual patient-to-patient behavior varies in the physiologic conditions exhibited during sleep disordered breathing, these variances are accounted for via calibration of an implantable pulse generator system (as described in association with at least FIGS. 4E-4H) such that the therapeutic stimulation regimen and detection model is tailored for each patient to ensure accuracy in identifying sleep disordered breathing for each particular patient. In some embodiments, when the sleep disordered breathing event is a central sleep apnea event, the substantial change in the amplitude of the sensed bio-impedance signal includes a substantial decrease in the amplitude of the sensed bio-impedance signal and the substantial change in the amplitude of the sensed respiratory pressure signal includes a substantial decrease in the amplitude of the sensed respiratory pressure signal. In other embodiments, the sleep disordered breathing event is a hypopnea event, and the substantial change in the amplitude of the sensed bio-impedance signal includes a substantial decrease in the amplitude of the sensed bio-impedance signal and the substantial change in the amplitude of the sensed respiratory pressure signal includes a substantial increase in the amplitude of the sensed respiratory pressure signal. However, in the case of the hypopnea event, the respective substantial decrease in the amplitude of the sensed bio-impedance signal and the respective substantial increase in the amplitude of the sensed respiratory pressure signal are of a lower magnitude change, respectively, than occur in an obstructive sleep apnea event.

Figure 7B:
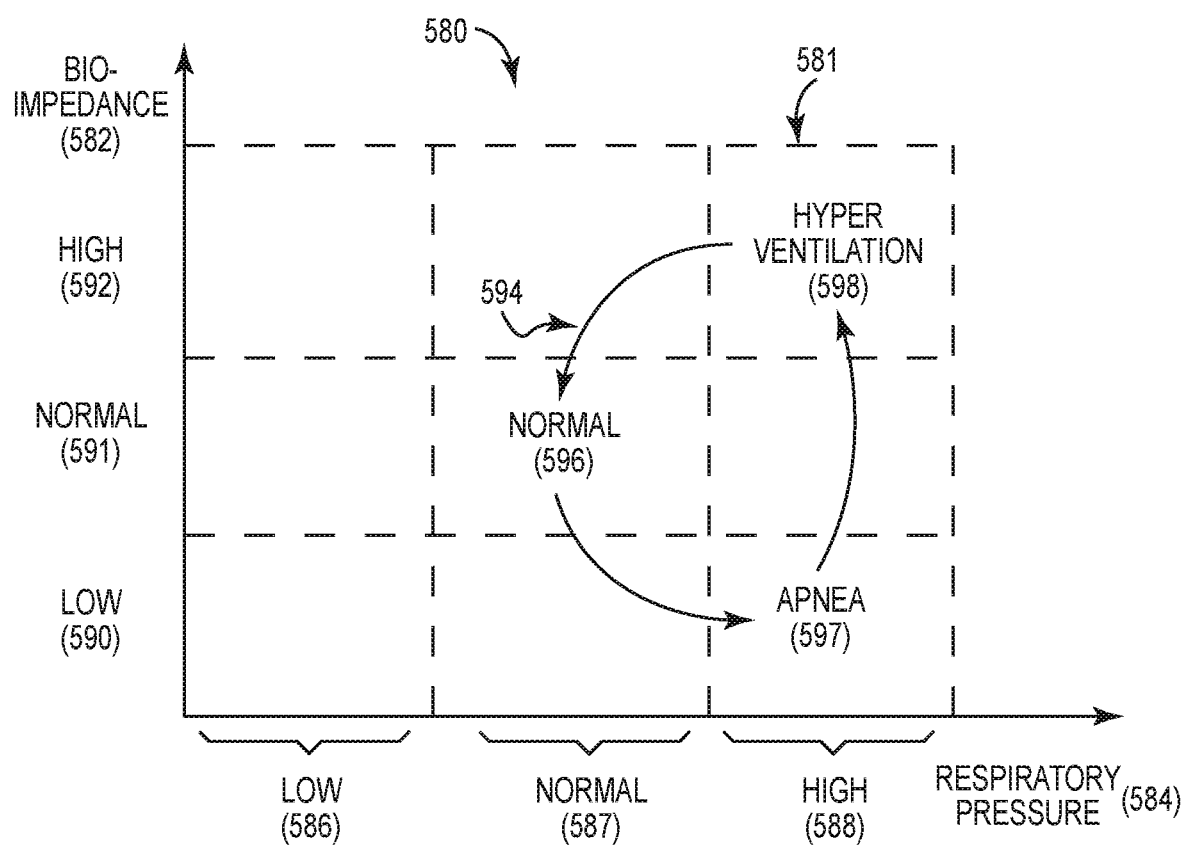
FIG. 7B is a graph schematically illustrating a grid of breathing states via mapping a bio-impedance signal relative to a respiratory pressure signal, according to an embodiment of the present disclosure.

In some embodiments, a method of detecting the presence of a sleep disordered breathing behavior includes mapping the bio-impedance signal relative to the respiratory pressure signal to identify whether a sleep disordered breathing behavior, and in particular, whether an obstructive sleep apnea has occurred. In one non-limiting example, FIG. 7B is a graph 580 that schematically illustrates different breathing patterns as a grid 581 based upon the bio-impedance signal 582 (y-axis) relative to the respiratory pressure signal 584 (x-axis). As illustrated in FIG. 7B, a combination of a normal amplitude 587 of respiratory pressures and a normal amplitude 591 of bio-impedance measurements indicate that normal breathing 596 is occurring.

However, as illustrated via graph 580 of FIG. 7B, as an obstructive sleep apnea (or hypopnea) develops, the bio-impedance and respiratory pressure signals move in the opposite directions, resulting in a combination of a high amplitude 588 of respiratory pressures and a low amplitude 590 of bio-impedance signals to indicate an obstructive sleep apnea 597. As the body responds to the obstructive sleep apnea via hyperventilation, a combination of a high amplitude 588 of respiratory pressures and a high amplitude 592 of bio-impedance signals indicates a high effort or hyperventilation pattern 598. For example, in FIG. 7A, hyperventilation is observable from the amplitude of respiration pressure (segment 564) being about twice the amplitude of respiration pressure during normal breathing (segment 560) and with the amplitude of bio-impedance during hyperventilation (segment 544) being substantially higher than the amplitude of bio-impedance during normal breathing (segment 540) or during the apneic event.

With these different breathing patterns in mind, graph 580 further illustrates a cycle 594 that moves from normal breathing (596) to apneic events (597) to hyperventilation (598) and then returning to normal breathing (596) as the obstruction lessens.

In some embodiments, in addition to monitoring the amplitude of hyperventilation following a sleep disordered breathing behavior, the system monitors a duration or length of a hyperventilation event. This duration also can be correlated to a level of oxygen desaturation caused by the preceding sleep disordered breathing event. In this manner, the duration of the hyperventilation event is used as at least one factor in determining a sleep disordered breathing severity score, with greater durations of hyperventilation being generally associated with, and representative of, more severe sleep disordered breathing and with lower durations of hyperventilation being representative of less severe sleep disordered breathing.

In some embodiments, a hyperventilation function (such as hyperventilation function 186 of therapy manager 106 in FIG. 3A) identifies a hyperventilation period following a sleep disordered breathing event via identifying a substantial change in the amplitude of the sensed bio-impedance signal after the sleep disordered breathing event. Moreover, in some embodiments, the hyperventilation function is configured to identify the hyperventilation period via a substantial change in an amplitude of the sensed respiratory pressure signal after the sleep disordered breathing event that occurs substantially simultaneously with the substantial change in the amplitude of the sensed bio-impedance signal after the sleep disordered breathing event. In some embodiments, the hyperventilation function is configured to identify, a severity of a sleep disordered breathing event preceding the hyperventilation period based on at least one of a duration of the hyperventilation period, a duration of the sleep disordered breathing event, or a lowest blood oxygen saturation following the sleep disordered breathing event.

In some embodiments, a method of detecting the presence of a sleep disordered breathing behavior includes tracking a percentage change in both the bio-impedance signal and the respiratory pressure signal to determine whether an sleep disordered breathing has occurred. For example, one can track the bio-impedance signal and the respiratory pressure signal during normal respiration to establish a baseline and then identify a percentage decrease (or an absolute decrease) in the bio-impedance signal and a percentage increase (or an absolute increase) in the respiratory pressure signal during a potential sleep disordered breathing event. If one or both of the respective percentage decrease (bio-impedance) and percentage increase (respiratory pressure) exceed a predetermined threshold (e.g., 50%, 75%, 100%, etc.), then the system concludes that an apnea/hypopnea event has taken place. As a further illustration, FIG. 7A provides a non-limiting example and illustrates that bio-impedance signal 504 decreased generally by 100% (represented by amplitude 0) in segment 542 (as compared to amplitude A in normal respiratory segment 540) and that respiratory pressure signal 552 increased generally by 100% (as represented by amplitude 2A) in segment 562 (as compared to amplitude A in normal respiratory segment 560). Assuming that the measurement comprises an average (100%) of the two respective percentage changes (100, and 100), and the threshold is a 90% change, then the 100% average change in the respective signals exceed the threshold (e.g., 90%) which indicates that an sleep disordered breathing event has occurred. The occurrence of this sleep disordered breathing event is modeled by the corresponding segment 532 of airflow signal 502.

In some embodiments, the threshold average percentage change is based on at least one of a minimum quantity of breaths, a minimum preset quantity of respiratory cycles, or a predetermined period of time including multiple respiratory cycles.

For these reasons, in accordance with the principles of the present disclosure, using a combination of the bio-impedance signal and the respiratory pressure signal enables a robust method of detecting apneas or hypopneas, which is less likely to produce a false positive identification of an apnea.

However, embodiments of the present disclosure are not limited to detecting an apnea (or hypopnea) solely through the use of the bio-impedance signal and/or the respiratory pressure signal. Other physiologic signals are known to provide an indication that apneas/hypopneas are occurring. These signals can be processed to further confirm that apneas/hypopneas are occurring to augment the approaches above. For example, a heart rate is known to decrease at the onset of an obstructive apnea, followed by a fast rise in heart rate toward the end of the apnea and immediately following the apnea. In another example, a blood oxygen level (measured optically via an implanted system) is known to drop during and following an apneic event. Accordingly, such physiologic data can be obtained via the sensing module 102 of the IPG 100 to further confirm the presence or absence of the apnea/and hypopnea. Moreover, in addition to the primary physiologic data of the respiratory pressure and the bio-impedance illustrated in FIG. 7A, the data from these physiologic signals (e.g., heart rate, blood oxygen) is additionally used to measure the duration and/or intensity of an apnea/hypopnea event, which provides an indication of the severity of the apnea/hypopnea event.

Figure 7C:
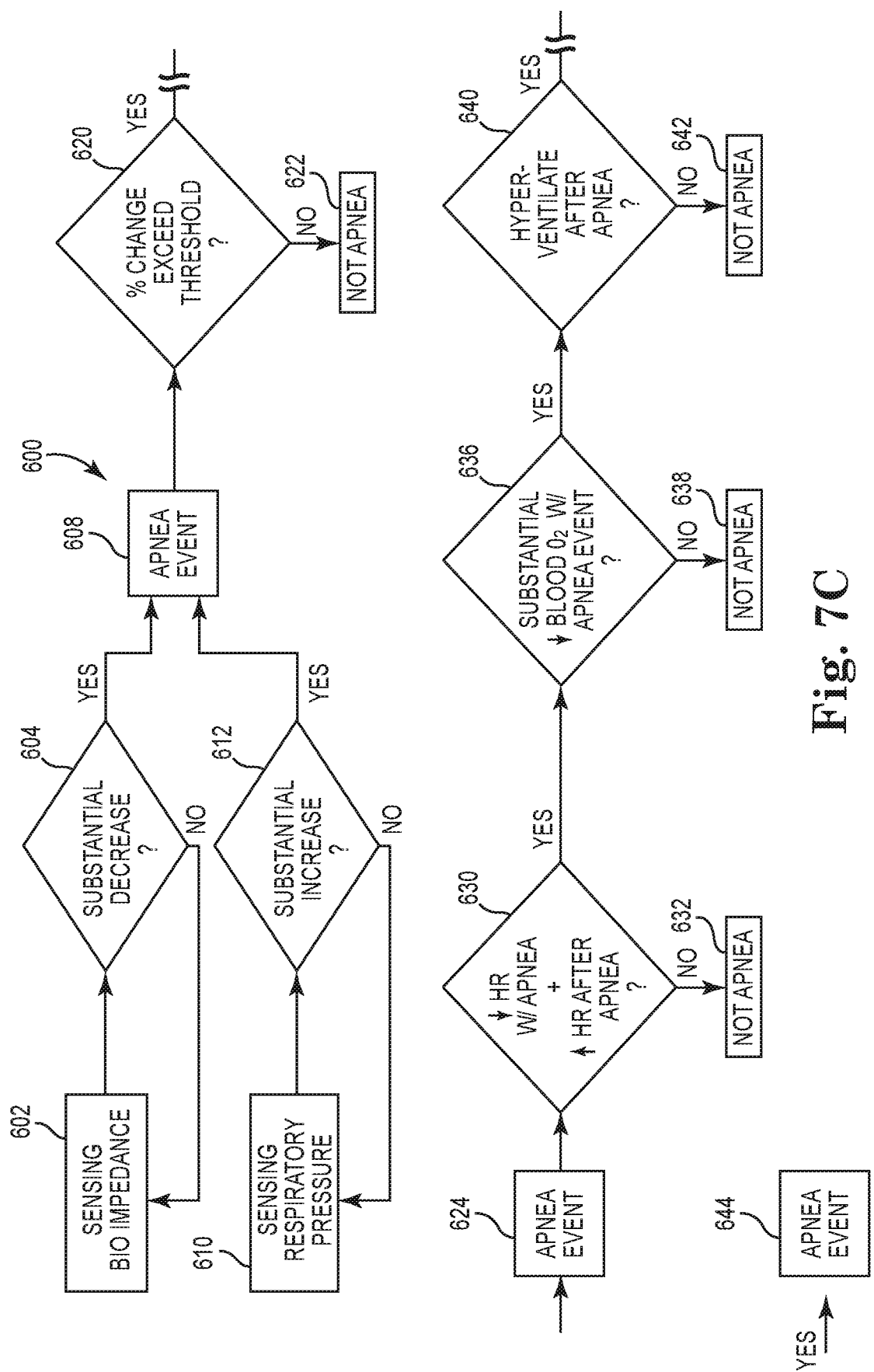
FIG. 7C is a flow diagram of a method of detecting sleep disordered breathing behavior, according to an embodiment of the present disclosure.

With these general principles in mind, FIG. 7C schematically illustrates a method 600 of identifying sleep disordered breathing behavior (such as an apnea even or hypopnea event), in accordance with an embodiment of the present disclosure. As illustrated in FIG. 7C, method 600 includes sensing a bio-impedance (at 602) and detecting whether a substantial change (such as substantial decrease) has occurred. At 610, method 600 includes sensing respiratory pressure and detecting whether a substantial change (e.g. increase) has occurred. If a substantial change in both the sensed bio-impedance and the sensed respiratory pressure is detected, then an apnea event (sleep disordered breathing) is identified at 608. However, additional thresholds can be used to further confirm the presence or absence of a sleep disordered breathing event. In some embodiments, as at 620, method 600 queries whether the percentage change in the sensed bio-impedance and/or the sensed respiratory pressure exceeds a threshold (e.g. a threshold percentage change). If not, the sensed behavior is determined not to be an apnea event (at 622). However, if the threshold is met or exceeded, then method confirms the presence of an apnea event at 624.

In some embodiments, further confirmation is provided in method 600 via observing, at 630, whether the sensed heart rate decreases during a portion of the potential apnea event and then increases after the potential apnea event. If not, then no apnea event occurred (at 632). However, if that heart rate behavior is confirmed, then further confirmation of an apnea event (i.e., sleep disordered breathing behavior) is provided. In some embodiments, further confirmation is provided in method 600, at 636, via observing a substantial decrease in blood oxygen saturation that substantially coincides with sleep disordered breathing behavior. If this observation is lacking, then method 600 could determine that no apnea event occurred 638. In some embodiments, further confirmation of sleep disordered breathing is made at 640 in method 600 via detecting hyperventilation after the potential apnea event. If the hyperventilation is not found, then no apnea event has occurred. However, if such hyperventilation is identified, then method confirms a presence of a sleep disordered breathing event or behavior. It will be understood that in some embodiments, the various confirmatory queries at 620, 630, 636, and 640 can be performed in any order or performed simultaneously, and that one or more of the particular queries can be omitted or other confirmatory queries based on physiologic conditions can be added.

Another embodiment of the present disclosure includes a system and method to automatically adjust the level of therapy to treat sleep disordered breathing behavior based on the measurement of AHI (Apnea Hypopnea Index) or another apnea severity index or scoring tool. With this system, the level of therapy will be automatically adjusted to match the needs of the patient, which are known to vary based on sleep state, body position, and other physiologic factors (e.g., alcohol use, sleepiness, etc.). Adjustments to the therapy include incrementing or decrementing the level of therapy, as described below in more detail. In addition, as will be apparent from the description below, this "auto-titration" system and method for automatically adjusting the level of therapy operates in a substantially different manner than conventional Continuous Positive Airway Pressure (CPAP) systems. Among other differences, an implantable neuro-stimulation system, in accordance with principles of the present disclosure, presents a substantially different type of approach to treating sleep disordered breathing behavior (such as, but not limited to obstructive sleep apneas). Consequently, the types of therapy parameters and control systems used in an implantable neuro-stimulation system are substantially different than the therapy parameters and control systems used in the CPAP systems.

Figure 8A:
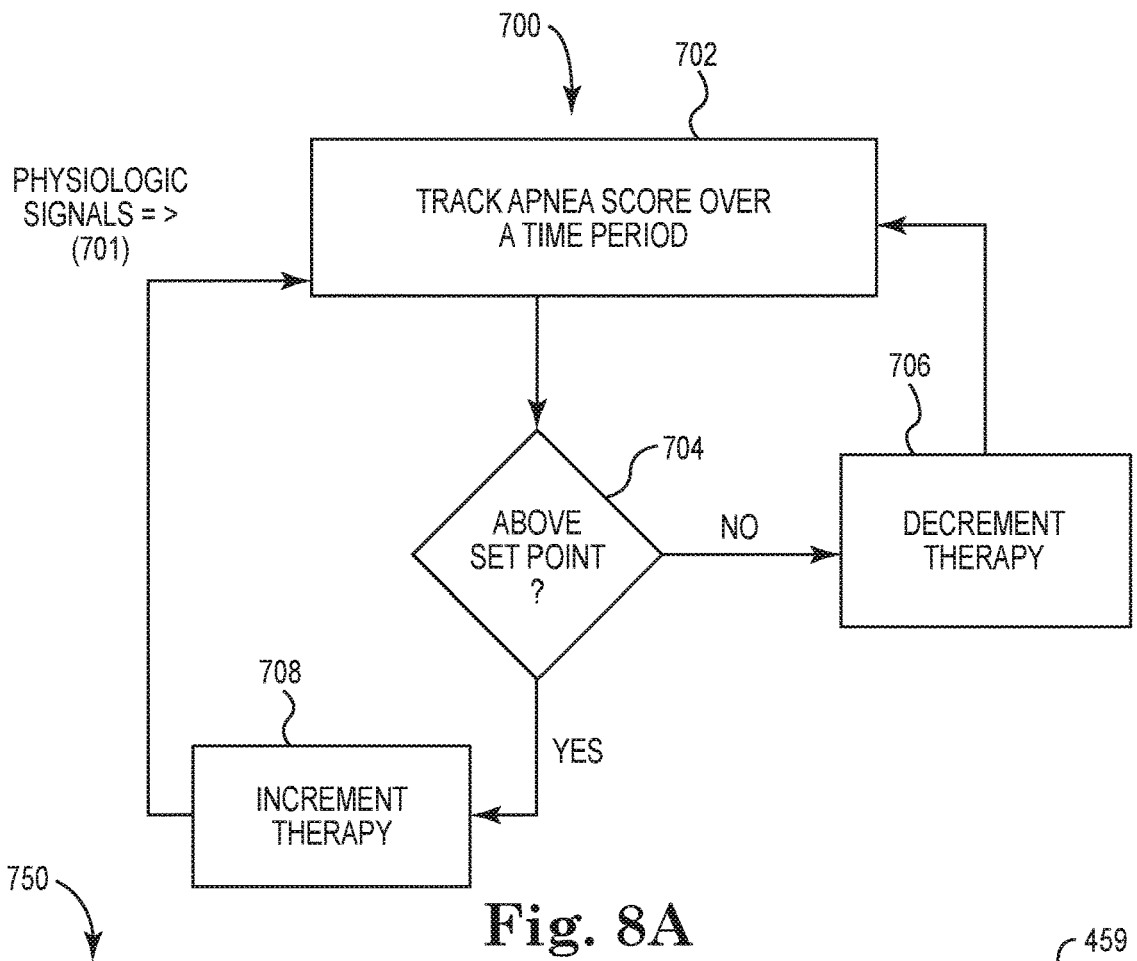
FIG. 8A is a flow diagram of a method of automatically adjusting the level of therapy, according to an embodiment of the present disclosure.

FIG. 8A is a flow diagram schematically illustrating a method 700 of automatically adjusting a level of therapy, in accordance with embodiments and principles of the present disclosure. In one embodiment, method 700 is performed using the systems, components and other methods previously described in association with FIGS. 1-7B. In other embodiments, method 700 is performed using other systems and components.

As shown in FIG. 8A, at box 702 method 700 includes measuring the number of apneas (AHI) or an apnea severity score over a time period to track the frequency of apnea/hypopnea events based on physiologic signals 701 provided via sensing module 102 of IPG 100. The method includes establishing a predetermined setpoint corresponding to an acceptable number of apneas/hypopneas over a period of time (e.g. number of apneas per hour) or a setpoint corresponding to an acceptable apnea severity score. In some embodiments, the set point is fixed while in other embodiments, the setpoint is programmable (e.g., 0, 1, 3, 5, 10 events/hour etc.). In another embodiment, in addition to counting the number of apneas/hypopneas within a given time period, the method also looks at the intensity and/or duration of one or more apnea events to determine whether the measured patient behavior is above or below a setpoint. In this latter embodiment, the number of apneas, the duration of an apnea, and intensity of apneas (as well as other physiologic data) are combined into a severity score. In one embodiment, the intensity of an apnea event is at least partially determined by a percentage decrease (or absolute measurement) of blood oxygen level, a change in heart rate, and/or a duration of hyperventilation following an apnea.

As shown at box 704, the system/method periodically queries whether or not the measured AHI (or other index) is above the predetermined set point. If the query at box 704 is answered affirmatively (i.e. yes), then too many apnea/hypopneas are occurring, and method 700 proceeds to increment or increase the level of therapy, as represented by box 708. As the level of therapy is increased, method 700 continues the ongoing measurements of the number of apnea events (or an apnea severity score), as represented by box 702.

On the other hand, if the query at box 704 is answered negatively (i.e. no), then the current level of therapy is considered to be at least adequately treating the apnea/hypopnea condition of the patient. However, it is possible that a lower level of therapy could still adequately treat the apnea/hypopnea condition of the patient. Using a lower level of therapy would be desirable to avoid potential fatigue of the target nerve, while also reducing the amount of power consumed by the IPG 100. Once the level of therapy is decremented (as represented by box 706), method 700 maintains its measurements of the number of apnea events (or an apnea severity score) to determine if an adequate level of therapy is being maintained.

In this way, method 700 continually assesses the level of therapy administered to the patient and then automatically implements an increment or a decrement in the level of therapy, as warranted, to prevent the patient from receiving unnecessary stimulation (i.e., preventing overstimulation) to the target nerve while ensuring that at least a therapeutic level of therapy is maintained. In one aspect, this method 700 also terminates all stimulation when no therapy is warranted for an extended period of time. In some embodiments, an incremental increase in the level of therapy is executed in steps that are substantially larger (e.g. 50%, 100%) than the steps in which the level of therapy is decremented. In other words, increases in the level of therapy are made more aggressively than decreases in therapy. With this arrangement, the method 700 moves more quickly to eliminate the apnea events but moves slower when attempting to find a lower beneficial level of therapy.

In one embodiment, the controller has either pre-determined or programmable maximum stimulation settings to prevent overstimulation to the target nerve or surrounding tissue, initiating a patient arousal, or inducing discomfort to the patient. These maximum levels may be programmed by a physician while conducting an office query of the functionality of the system. In this way, boundaries are established for the auto-titrate method such that the parameters of therapy generally remain within the limits of comfort of most patients. Moreover, in some embodiments, the method 700 includes a patient override function (represented as patient override function 459 in FIG. 9) configured to enable the patient to override the method of automatic therapy to reduce the level (amplitude, duration, etc.) of therapy when the therapy is not comfortable for the patient. In some embodiments, this function is available by the increase/decrease function 250 of patient programmer 230, as previously described in association with FIG. 2.

Figure 8B:
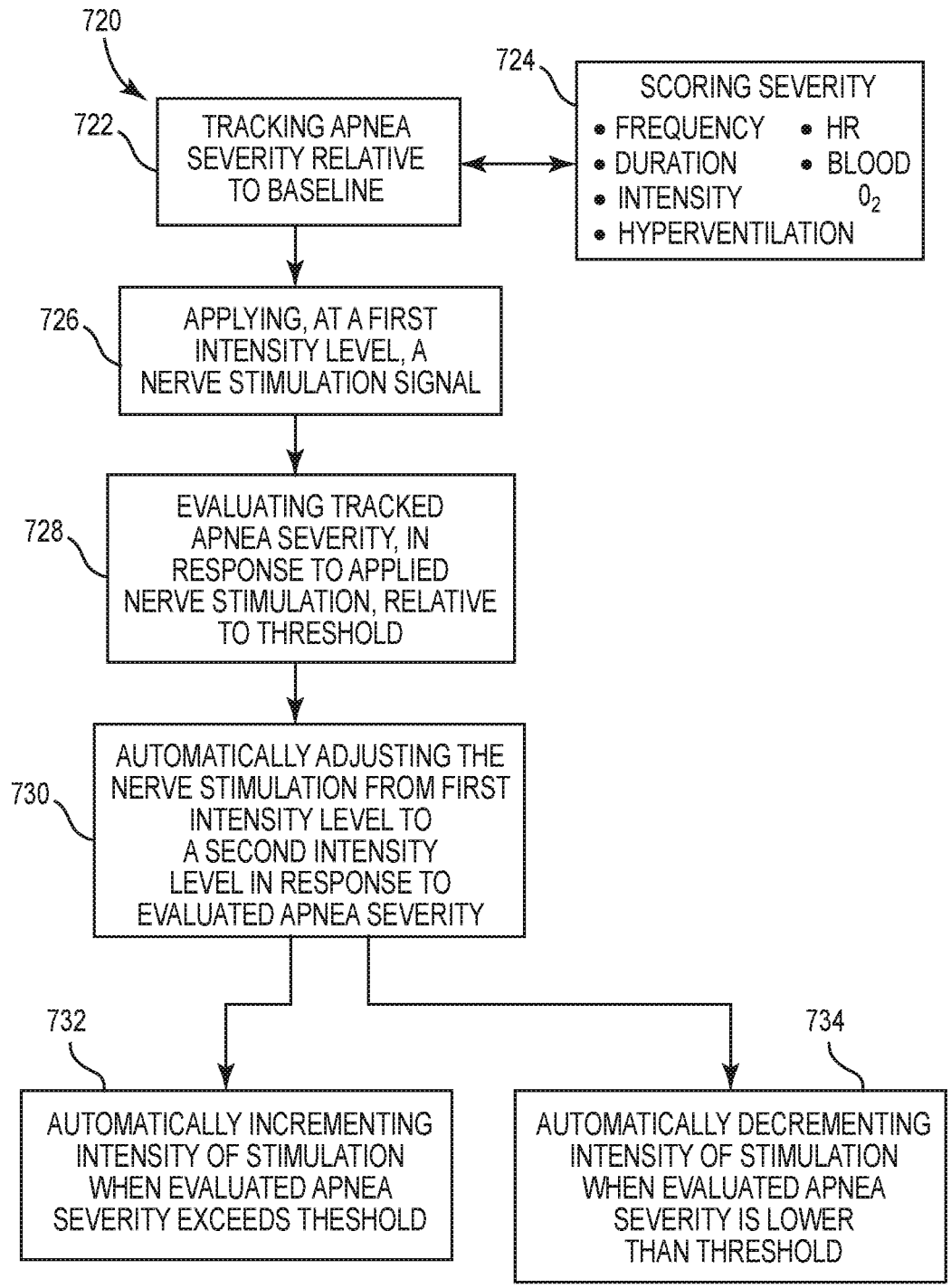
FIG. 8B is a flow diagram of a method of automatically adjusting a level of therapy, according to an embodiment of the present disclosure.

FIG. 8B further illustrates a method 720 of automatically adjustable therapy to treat sleep disordered breathing, according to an embodiment of the present disclosure. As illustrated in FIG. 8B, at 722 method 720 includes tracking a severity of sleep disordered breathing behavior relative to a baseline. This severity is based on one or more of a frequency of the sleep disordered breathing (SDB) events, a duration of the respective SDB events, an intensity of the respective SDB events, a presence of hyperventilation (as well as it duration or intensity), a change in heart rate, and/or a change in blood oxygen saturation.

At 726, method 720 includes applying, at a first intensity level, a nerve stimulation signal to an airway-patency related nerve. At 728, method 720 includes evaluating the tracked severity of the SDB behavior, in response to the applied nerve stimulation, relative to threshold. The nerve stimulation regimen is automatically adjusted, at 730, from the first intensity level to a second intensity level in response to the evaluated severity of the SDB behavior. This adjustment takes place either at 732 as an automatic incrementing of the intensity level of nerve stimulation when the evaluated SDB severity meets or exceeds a threshold or at 734 as an automatic decrementing of the intensity level of nerve stimulation when the evaluated SDB severity falls below that threshold.

In some embodiments, method 700 of automatically applying a therapy is at least partially governed by a stimulation goodness function. In particular, a setpoint is selected, monitored and adjusted dynamically according to a stimulation goodness function that balances at least the factors of patient comfort (based on feedback via the patient programmer or clinician programmer), therapeutic efficacy, and longevity. In one embodiment, the stimulation goodness function operates in a manner illustrated by FIG. 10.

Figure 10:
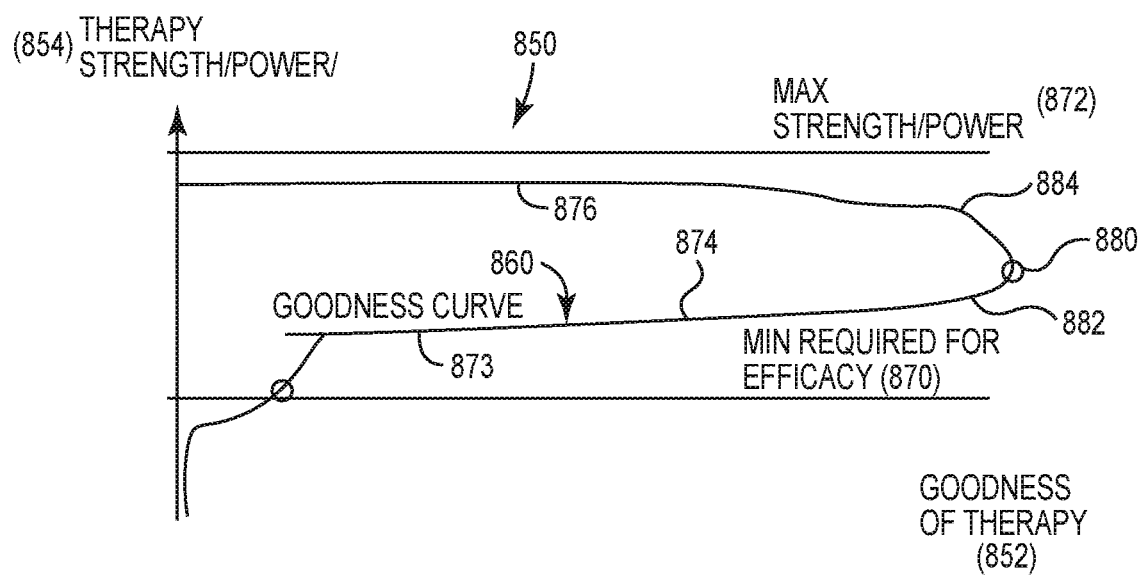
FIG. 10 is a graph schematically illustrating a stimulation goodness function applied in a method of treating apneas, according to an embodiment of the present disclosure.

FIG. 10 schematically illustrates a method of automatically adjusting a setpoint in which increasing amounts of therapeutic stimulation 854 (y-axis) are mapped relative to a goodness parameter 852 of the therapy (x-axis). Increasing amounts of goodness correspond to increased levels of patient comfort, longevity of the device, and therapeutic efficacy in reducing the number or severity of apneic events. As shown in FIG. 10, graph 850 depicts a stimulation goodness profile 860 and also identifies an upper limit 872 on the strength or power of stimulation (854) applied to the target nerve and a lower limit 570 on the strength or power of stimulation required to achieve a minimum level of efficacious treatment. In some embodiments, one or both of the lower limit and the upper limit corresponds to a physician defined setpoint while in other embodiments, one or both of the lower limit and the upper limit corresponds to a manufactured defined setpoint. Alternatively, the upper limit and/or the lower limit are determined algorithmically through monitoring apnea events and/or patient commands.

As can be seen from FIG. 10, at lower amounts of strength/power, the measured goodness (852) is relatively low (shown at 873) and with increasing amounts of strength/power, the measured goodness gradually increases (shown by segments 874 and 882) providing a better therapeutic experience for the patient until an optimum point 880 is achieved. At this point, any further increases in strength/power will cause a gradual decrease in measured goodness (shown by segment 884) for the patient as further increases in strength/power is applied. In other words, the optimum point 880 represents the point above the minimum strength/power that provides the greatest overall benefit to the patient while any further increases in strength/power reduce the overall benefit to the patient, i.e., the point of diminishing returns. In other words, any increases in the intensity of stimulation beyond point 880 will result in a decrease in patient comfort, an increase in energy usage, and/or a decrease in efficacy. Accordingly, by implementing a stimulation goodness function, small dynamic increases in the level of stimulation above a minimum limit and/or physician-defined settings can lead to a large increase in the overall benefit to the patient. On the other hand, when the setpoint is too high, the stimulation goodness function can dynamically guide the setpoint to a lower value to increase the overall benefit to the patient.

In one embodiment, the level of therapy can be incremented or decremented via the auto-titrate module 170 (and the treatment parameters module 168) of the therapy manager 106 of IPG 100 shown in FIG. 3A. In this regard, FIG. 9 is a block diagram schematically illustrating additional features and attributes of the auto-titrate module 170 (and the treatment parameters module 168) that is employed in accordance with the method 700 of automatically adjusting a level of therapy to treat sleep disordered breathing behavior.

Figure 9:
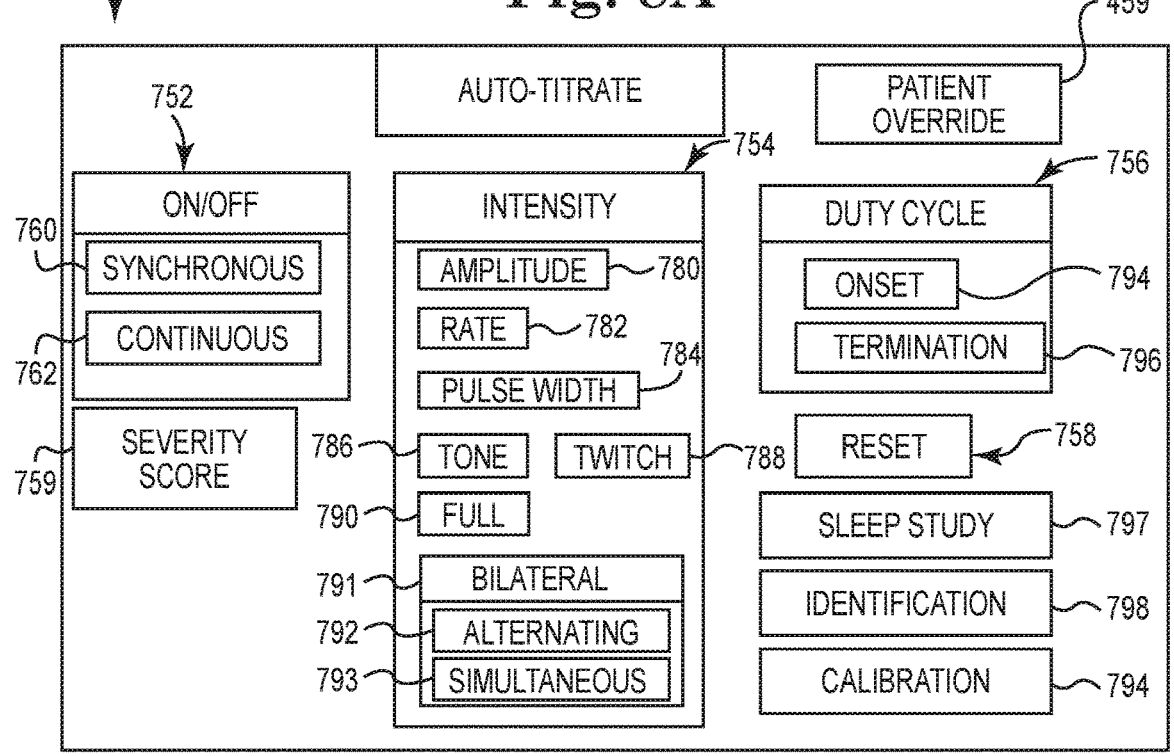
FIG. 9 is a block diagram of an auto-titrate module of a system for treating sleep disordered breathing behavior, according to an embodiment of the present disclosure.

As illustrated in FIG. 9, the auto-titrate module 750 is configured to maintain, increment, or decrement the level of therapy in accordance with method 700 illustrated by FIG. 8A. In one embodiment, the auto-titrate module 750 includes one or more of the following functions and modules including: an on/off module 752; an intensity module 754; a duty cycle module 756; a reset module 758; a patient override function 459, and a sleep study parameter 797.

In one embodiment, the On/Off module 752 is configured to activate or deactivate stimulation to the target nerves/muscles of the upper airway (that restores airway patency). In one aspect, an "Off" state of module 752 corresponds to first state 202 or second state 204 of system 200 (see FIG. 4A) in which the IPG 100 monitors the body motion or activity of the patient or is configured to detect apneas but a state in which no stimulation is applied. However, an "On" state of module 752 directly corresponds to third state 206 of system 200 in which a stimulation therapy is to be applied to the patient.

Moreover, when this On/Off module 752 is in an "On" state, stimulation to the target nerve may be applied continuously or synchronized (via stimulation module 104 of IPG 100—FIG. 3A) with respiration/inspiration in accordance with a continuous parameter 762 and a synchronous parameter 760, respectively. In another aspect, the intensity module 754 selects an amplitude (parameter 780), a rate (parameter 782), and/or a pulse width (parameter 784) of the stimulation signal to the target nerve to achieve a desired level of nerve recruitment. It is also understood that in some embodiments the intensity module 754 includes, or can operate in coordination with, a multisite parameter 194A, bilateral parameter 194B, and fascicle parameter 194C, as previously described in association with IPG 100 of FIG. 3A. Moreover, intensity module 754 is configured to further modulate the stimulation intensity by applying a sub-threshold intensity that provides minor tone to the innervated muscle (as represented by tone parameter 786), a twitch intensity (represented by twitch parameter 788), and/or varying levels of nerve/muscle recruitment all the way up to full nerve/muscle recruitment (as represented by full parameter 790).

In one embodiment, the auto-titrate module 750 is self-learning. In other words, by using a predetermined order of parameter adjustments to adjust the amplitude, rate, and/or pulse width of stimulation (i.e., stimulation parameter settings), a desired level of nerve recruitment is achieved. In some embodiments, this predetermined order is automatically used prior to obtaining data in response to a therapy on a given patient and may be based on statistical analysis of a population of patients. In use, the auto-titrate module 750 will monitor the available sensing and stimulation parameters, evaluate the response to therapy (using the predetermined order/level of settings) for a given patient, and then identify (and implement) the optimal settings for stimulation therapy. In another aspect, the auto-titrate module 750 iteratively repeats the process of applying the most recently determined optimal parameter settings, evaluates the therapy response, and adjusts the parameter settings. In this way, the auto-titrate module 750 self learns the best therapy setting as the therapy is applied over a period of time.

In one embodiment, as previously described, the auto-titrate module 750 includes a sleep study parameter 797 configured to direct that the IPG 100 (as part of system 200 and/or method 700) implanted within the patient learn therapy parameters for that particular patient in coordination with a polysomnograph or other sleep study system. In this arrangement, the sensing module 102 of IPG 100 (FIG. 2) is active during the sleep study so that parameters sensed via IPG 100 are correlated with, and calibrated, relative to known sleep study parameters that are indicative of various apnea-related physiologic events, patterns, and behaviors. A few examples of such correlation was previously described in association with FIG. 4E, Accordingly, via the sleep study the IPG 100 learns a patient's physiologic patterns surrounding an apnea event, which helps to establish a baseline or initial set of stimulation therapy settings for auto-titrate module 750 (as part of system 200 and method 700). After this baseline is established, the system 200 and/or method 700 operates in substantially the same manner previously described in association with at least FIGS. 1-8.

In some embodiments, the auto-titrate module 750 also includes a stimulation duty cycle module 756 that manages the duration of the stimulation time, including the amount of time the stimulation starts before inspiration onset or after inspiration onset, as the timing of this onset (as represented by onset parameter 794) is known to affect the aggressiveness and effectiveness of the therapy. For example, starting stimulation after the onset of inspiration may be ineffective due to the airway obstructing prior to stimulation (and once obstructed stimulation may not be capable of overcoming the obstruction). However, starting stimulation well in advance of inspiration onset may be beneficial in preventing flow restriction or full obstruction by providing stimulation before the airway closes. Accordingly, one method of treatment includes triggering stimulation of the target nerve prior to inspiration onset. One patent describing the time period surrounding inspiration onset (in relation to triggering stimulation of a nerve to treat apnea) is Christopherson U.S. Pat. No. 5,944,680, titled RESPIRATORY EFFORT DETECTION METHOD AND APPARATUSES, and which is hereby incorporated by reference in its entirety. In another aspect, an incomplete emptying of the lungs will reduce the volume of fresh air that can be inspired in the next breath. Accordingly, in some embodiments, the duty cycle module 756 includes a termination parameter 796 that controls the timing of stimulation turn-off (i.e., termination) before or after the end of inspiration.

Referring again to FIG. 9, in some embodiments of the present disclosure, auto-titrate module 750 includes a reset module 758. In general terms, the reset module 758 is configured to facilitate synchronizing stimulation of the upper airway with respiration. Signal processing of the respiration waveform can become challenging during cycles of apneas or hypopneas, primarily due to the widely varied morphologies of the respiratory signals. Yet, once stable synchronization of the stimulation with the respiratory waveform is achieved, apneas/hypopneas are readily prevented.

Accordingly, in light of the difficulty in performing such signal processing during the cycles of apneas/hypopneas, in this one embodiment, the reset module 758 applies (during the cycles of apneas/hypopneas) a substantially continuous or continuous burst of stimulation (or other predetermined time period) that effectively "resets" the patient to stable respiration. In some embodiments, this burst of stimulation can last about twenty seconds. In one embodiment, the substantially continuous burst of stimulation lasts a first time period greater than a duration of two nominal respiration cycles. During this reset, the system can better synchronize the stimulation with respiration because the patient is in a non-apneic period of respiration. This "reset" stimulation allows several unobstructed breaths to occur and allows the signal processing to track a stable respiratory signal. After the reset, each separate application of stimulation is limited to a duration corresponding to a portion (or fraction) of a single respiratory cycle (according to the methods of treatment and embodiments of the present disclosure previously described herein) to ensure that nerve/muscle fatigue does not occur. In one embodiment, the reset module 758 also tracks the respiratory pressure signal during the reset mode to observe the efficacy of the substantially continuous burst of stimulation.

In another embodiment, when consistent respiratory information cannot be obtained because of a noisy environment (or for other reasons), stimulation is completely suspended until suitable respiratory information is obtainable or stimulation is converted to an alternate stimulation having a fixed, intermittent duty cycle. In one non-limiting example, the alternate stimulation has a duty cycle of 2 seconds stimulation separated by 3 second periods of no stimulation.

In another embodiment, a bilateral function 791 of auto-titrate module 750 (such as auto-titrate module 170 of therapy manager 106 in FIG. 3A) cooperates with the bilateral parameter 194B of stimulation module 104 (FIG. 3A) to determine whether to alternately (via function 792) or simultaneously (via function 793) stimulate the left side and right side of the body. Moreover, when used in conjunction with the multi-site parameter 194A of stimulation module 104 (FIG. 3A), the auto-titrate module 750 also determines whether to simultaneously or alternately stimulate different sites along one or more nerves, whether on the left side or the right side of the body.

While at least one exemplary embodiment has been presented in the foregoing detailed description, it should be appreciated that variations exist. It should also be appreciated that the exemplary embodiment or exemplary embodiments are only examples, and are not intended to limit the scope, applicability, or configuration of the present disclosure in any way. Rather, the foregoing detailed description will provide those skilled in the art with a convenient road map for implementing the exemplary embodiment or exemplary embodiments. It should be understood that various changes can be made in the function and arrangement of elements without departing from the scope of the present disclosure as set forth in the appended claims and the legal equivalents thereof.

The invention claimed is:

1. A method comprising:
applying, during a sleep period, electrical stimulation therapy via an implantable non-cardiac pulse generator and a non-cardiac electrode relative to a hypoglossal nerve to treat obstructive sleep apnea via at least tongue protrusion; and
assessing, via the non-cardiac pulse generator and at least during the sleep period, an effectiveness of the electrical stimulation therapy in relation to a level of the electrical stimulation therapy applied via the non-cardiac pulse generator in treating obstructive sleep apnea.

2. The method of claim 1, wherein assessing the effectiveness of the electrical stimulation therapy comprises:
continually assessing, during the sleep period, the effectiveness of the electrical stimulation therapy in relation to the level of electrical stimulation therapy in treating obstructive sleep apnea.

3. The method of claim 2, comprising:
performing the continual assessing, during the sleep period, of the effectiveness of the electrical stimulation therapy in relation to the level of electrical stimulation therapy in treating obstructive sleep apnea while maintaining application of the electrical stimulation therapy.

4. The method of claim 3, wherein the continually assessing, during the sleep period, the effectiveness of the electrical stimulation therapy in relation to the level of electrical stimulation therapy in treating obstructive sleep apnea comprises monitoring a number of apneas.

5. The method of claim 1, wherein the assessing, during the sleep period, the effectiveness of the electrical stimulation therapy in relation to the level of electrical stimulation therapy in treating obstructive sleep apnea comprises:
monitoring an apnea score based on sensing at least one of a number of apneas, a duration of apneas, and an intensity of apneas.

6. The method of claim 1, comprising:
adjusting the level of electrical stimulation therapy in treating obstructive sleep apnea based on the assessed effectiveness of the electrical stimulation therapy.

7. The method of claim 6, wherein adjusting the level comprises selecting between:
increasing the level of the electrical stimulation therapy when the assessment indicates the number of apneas exceeds a setpoint; and
maintaining or decreasing the level of the electrical stimulation therapy when the assessment indicates the number of apneas is at or less than a setpoint.

8. The method of claim 6, comprising:
continually assessing, during the sleep period, the effectiveness of the electrical stimulation therapy while adjusting the level of the electrical stimulation therapy.

9. The method of claim 8, wherein adjusting the level of the electrical stimulation therapy comprises:
increasing the level of the electrical stimulation therapy up to a maximum setting.

10. The method of claim 9, wherein the maximum setting corresponds to a level of the electrical stimulation therapy at which patient arousal would be initiated.

11. The method of claim 8, wherein the continually assessing comprises:
performing ongoing measurements of the number of apneas and terminating the application of the electrical stimulation therapy when the assessment indicates the number of apnea events is less than a setpoint.

12. The method of claim 8, wherein the continually assessing also comprises:
assessing the level of the electrical stimulation therapy according to an apnea score, which is at least based on the number of apneas, the duration of apneas, and intensity of apneas.

13. The method of claim 1, wherein assessing the effectiveness of the electrical stimulation therapy comprises:
via an accelerometer, sensing physiologic information comprising respiratory information.

14. A method comprising:
applying, during a sleep period, electrical stimulation therapy via an implantable non-cardiac pulse generator and a non-cardiac electrode relative to a hypoglossal nerve to treat obstructive sleep apnea via at least tongue protrusion; and
continually assessing, via the non-cardiac pulse generator and at least during the sleep period, an effectiveness of the electrical stimulation therapy in relation to a level of the electrical stimulation therapy applied via the non-cardiac pulse generator to treat obstructive sleep apnea while maintaining application of the electrical stimulation therapy,
wherein the continual assessing, during the sleep period, the effectiveness of the electrical stimulation therapy in relation to the level of the electrical stimulation therapy to treat obstructive sleep apnea comprises determining respiratory information via acoustically sensing cardiac activity.

15. A method comprising:
applying, during a sleep period, electrical stimulation therapy via an implantable non-cardiac pulse generator and a non-cardiac electrode relative to a hypoglossal nerve to treat obstructive sleep apnea via at least tongue protrusion; and
assessing, via the non-cardiac pulse generator and at least during the sleep period, an effectiveness of the electrical stimulation therapy in relation to a level of the electrical stimulation therapy applied via the non-cardiac pulse generator,
wherein assessing the effectiveness of the electrical stimulation therapy in relation to the level of electrical stimulation therapy comprises:
counting a number of apnea events based on a heart rate.

16. A method comprising:
applying, during a sleep period, an electrical stimulation signal from an implantable non-cardiac pulse generator through at least one electrode to a hypoglossal nerve to stimulate at least one upper-airway patency-related muscle to increase upper airway patency at least until a number of obstructive sleep apnea events changes from a first level to a second level as assessed via the implantable non-cardiac pulse generator; and
continually assessing an effectiveness of the electrical stimulation signal as the number of obstructive sleep apnea events during the sleep period while applying the electrical stimulation signal.

17. The method of claim 16, wherein the second level is less than the first level, and the method comprises:
decreasing application of the electrical stimulation signal during the sleep period while the number of obstructive sleep apnea events is maintained at or below the second level.

18. The method of claim 17, wherein decreasing application of the electrical stimulation signal during the sleep period comprises decreasing at least one of:
   a duration of the applied electrical stimulation signal;
   a frequency of the applied electrical stimulation signal; and
   an amplitude of the applied electrical stimulation signal.

19. The method of claim 17, wherein decreasing the application during the sleep period comprises:
   terminating application of the electrical stimulation signal when the number of obstructive sleep apnea events is at or below the second level.

20. The method of claim 16, wherein the continually assessing during the sleep period comprises on-going monitoring of sensed physiologic conditions.

21. The method of claim 20, wherein the on-going monitoring of sensed physiologic conditions includes a duration of the respective obstructive sleep apnea events and an intensity of the respective obstructive sleep apnea events.

22. The method of claim 16, wherein the first level is greater than the second level, and comprising:
   increasing application of the electrical stimulation signal during the sleep period to cause the number of obstructive sleep apnea events to decrease from the first level to the second level.

23. The method of claim 16, wherein application of the electrical stimulation signal comprises:
   stimulating the hypoglossal nerve solely during the inspiratory phase of a respiratory cycle.

* * * * *